United States Patent
Scheltienne et al.

(10) Patent No.: US 12,415,079 B2
(45) Date of Patent: Sep. 16, 2025

(54) NEUROMODULATION SYSTEM

(71) Applicant: ONWARD MEDICAL N.V., Eindhoven (NL)

(72) Inventors: Mathieu Scheltienne, Eindhoven (NL); Jeroen Tol, Eindhoven (NL); Robin Brouns, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 0 days.

(21) Appl. No.: 17/897,739

(22) Filed: Aug. 29, 2022

(65) Prior Publication Data

US 2022/0409906 A1     Dec. 29, 2022

Related U.S. Application Data

(63) Continuation of application No. 17/105,345, filed on Nov. 25, 2020, now Pat. No. 11,491,336.

(30) Foreign Application Priority Data

Nov. 27, 2019    (EP) ..................................... 19211738

(51) Int. Cl.
     *A61N 1/36*          (2006.01)

(52) U.S. Cl.
     CPC ..... *A61N 1/36192* (2013.01); *A61N 1/36067* (2013.01); *A61N 1/36142* (2013.01);
     (Continued)

(58) Field of Classification Search
     CPC .............. A61N 1/3603; A61N 1/36067; A61N 1/36128; A61N 1/36142; A61N 1/36175;
     (Continued)

(56) References Cited

U.S. PATENT DOCUMENTS

| | | |
|---|---|---|
| 2,868,343 A | 1/1959 | Sproul |
| 3,543,761 A | 12/1970 | Bradley |
| | (Continued) | |

FOREIGN PATENT DOCUMENTS

| | | |
|---|---|---|
| AU | 2012204526 | 9/2016 |
| CA | 2649663 A1 | 11/2007 |
| | (Continued) | |

OTHER PUBLICATIONS

Abernethy, J. et al., "Competing in the Dark: An Efficient Algorithm for Bandit Linear Optimization", Conference on Learning Theory, (2008), 13 pages.

(Continued)

*Primary Examiner* — Amanda K Hulbert
(74) *Attorney, Agent, or Firm* — Finnegan, Henderson, Farabow, Garrett & Dunner, LLP

(57) ABSTRACT

A neuromodulation system including at least one input module for inputting a planned neuromodulation event or a series of neuromodulation events and at least one analyzing module for analyzing a neuromodulation event or a series of neuromodulation events.

The analyzing module and the input module may be connected such that the input module is configured to forward the planned neuromodulation event or a series of neuromodulation events to the analyzing module and the analyzing module is configured to analyze the planned neuromodulation event or a series of neuromodulation events regarding one or more possible neuromodulation conflict(s).

12 Claims, 12 Drawing Sheets

(52) U.S. Cl.
CPC ..... *A61N 1/36175* (2013.01); *A61N 1/36178* (2013.01); *A61N 1/36196* (2013.01)

(58) Field of Classification Search
CPC ............ A61N 1/36178; A61N 1/36192; A61N 1/36196; A61N 1/37235; A61N 1/37247; G16H 20/30; G16H 40/63
See application file for complete search history.

(56) References Cited

U.S. PATENT DOCUMENTS

| | | |
|---|---|---|
| 3,650,277 A | 3/1972 | Sjostrand et al. |
| 3,653,518 A | 4/1972 | Polen |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,303,904 A | 12/1981 | Chasek |
| 4,340,063 A | 7/1982 | Maurer |
| 4,340,216 A | 7/1982 | Murphy |
| 4,356,902 A | 11/1982 | Murphy |
| 4,379,462 A | 4/1983 | Borkan et al. |
| 4,398,537 A | 8/1983 | Holmbo |
| 4,402,501 A | 9/1983 | Lohman |
| 4,410,175 A | 10/1983 | Shamp |
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,574,789 A | 3/1986 | Forster |
| 4,724,842 A | 2/1988 | Charters |
| 4,742,054 A | 5/1988 | Naftchi |
| 4,784,420 A | 11/1988 | Makino et al. |
| 4,798,982 A | 1/1989 | Voorman |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,018,631 A | 5/1991 | Reimer |
| 5,031,618 A | 7/1991 | Mullet |
| 5,066,272 A | 11/1991 | Eaton et al. |
| 5,081,989 A | 1/1992 | Graupe et al. |
| 5,121,754 A | 6/1992 | Mullett |
| 5,284,151 A | 2/1994 | Onoda |
| 5,337,908 A | 8/1994 | Beck, Jr. |
| 5,344,439 A | 9/1994 | Otten |
| 5,348,544 A | 9/1994 | Sweeney et al. |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,421,783 A | 6/1995 | Kockelman et al. |
| 5,441,465 A | 8/1995 | Hefner et al. |
| 5,443,486 A | 8/1995 | Hrdlicka et al. |
| 5,476,441 A | 12/1995 | Durfee et al. |
| 5,562,718 A | 10/1996 | Palermo |
| 5,571,141 A | 11/1996 | McNeil et al. |
| 5,584,818 A | 12/1996 | Morrison |
| 5,601,527 A | 2/1997 | Selkowitz |
| 5,626,540 A | 5/1997 | Hall |
| 5,630,836 A | 5/1997 | Prem et al. |
| 5,643,330 A | 7/1997 | Holsheimer et al. |
| 5,643,332 A | 7/1997 | Stein |
| 5,667,461 A | 9/1997 | Hall |
| 5,733,322 A | 3/1998 | Starkebaum |
| 5,788,606 A | 8/1998 | Rich |
| 5,814,018 A | 9/1998 | Elson et al. |
| 5,819,962 A | 10/1998 | Okubo et al. |
| 5,876,425 A | 3/1999 | Gord et al. |
| 5,877,183 A | 3/1999 | Cincotta |
| 5,948,004 A | 9/1999 | Weijand et al. |
| 5,958,933 A | 9/1999 | Naftchi |
| 5,983,141 A | 11/1999 | Sluijter et al. |
| 6,052,624 A | 4/2000 | Mann |
| 6,058,331 A | 5/2000 | King |
| 6,066,163 A | 5/2000 | John |
| 6,080,087 A | 6/2000 | Bingham |
| 6,104,957 A | 8/2000 | Alo et al. |
| 6,115,634 A | 9/2000 | Donders et al. |
| 6,122,548 A | 9/2000 | Starkebaum et al. |
| 6,139,475 A | 10/2000 | Bessler et al. |
| 6,168,948 B1 | 1/2001 | Anderson et al. |
| 6,182,843 B1 | 2/2001 | Tax et al. |
| 6,188,927 B1 | 2/2001 | Lu et al. |
| 6,236,892 B1 | 5/2001 | Feler |
| 6,280,640 B1 | 8/2001 | Hurwitz et al. |
| 6,281,207 B1 | 8/2001 | Richter et al. |
| 6,308,103 B1 | 10/2001 | Gielen |
| 6,309,401 B1 | 10/2001 | Redko et al. |
| 6,319,241 B1 | 11/2001 | King et al. |
| 6,463,327 B1 | 10/2002 | Lurie et al. |
| 6,464,208 B1 | 10/2002 | Smith |
| 6,470,213 B1 | 10/2002 | Alley |
| 6,490,486 B1 | 12/2002 | Bradley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,901,292 B2 | 5/2005 | Hrdlicka et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,978,181 B1 | 12/2005 | Snell |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,099,718 B1 | 8/2006 | Thacker et al. |
| 7,110,820 B2 | 9/2006 | Tcheng et al. |
| 7,125,388 B1 | 10/2006 | Reinkensmeyer et al. |
| 7,127,287 B2 | 10/2006 | Duncan et al. |
| 7,127,296 B2 | 10/2006 | Bradley |
| 7,127,297 B2 | 10/2006 | Law et al. |
| 7,135,497 B1 | 11/2006 | Zeman et al. |
| 7,146,221 B2 | 12/2006 | Krulevitch et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,330,762 B2 | 2/2008 | Boveja et al. |
| 7,337,005 B2 | 2/2008 | Kim et al. |
| 7,337,006 B2 | 2/2008 | Kim et al. |
| 7,340,298 B1 | 3/2008 | Barbut |
| 7,377,006 B2 | 5/2008 | Genoa et al. |

(56) References Cited

U.S. PATENT DOCUMENTS

| | | |
|---|---|---|
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| D594,024 S | 6/2009 | King |
| D595,308 S | 6/2009 | King |
| 7,544,185 B2 | 6/2009 | Bengtsson |
| 7,565,195 B1 | 7/2009 | Kroll et al. |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | de Ridder |
| 7,734,351 B2 | 6/2010 | Testerman et al. |
| 7,742,037 B2 | 6/2010 | Sako et al. |
| 7,769,463 B2 | 8/2010 | Katsnelson |
| 7,769,464 B2 | 8/2010 | Gerber et al. |
| 7,780,617 B2 | 8/2010 | Tornatore et al. |
| 7,797,057 B2 | 9/2010 | Harris |
| 7,801,600 B1 | 9/2010 | Carbunaru et al. |
| 7,801,601 B2 | 9/2010 | Maschino et al. |
| 7,813,803 B2 | 10/2010 | Heruth et al. |
| 7,813,809 B2 | 10/2010 | Strother et al. |
| 7,840,270 B2 | 11/2010 | Ignagni et al. |
| 7,856,264 B2 | 12/2010 | Firlik et al. |
| 7,861,872 B2 | 1/2011 | Ng et al. |
| 7,877,146 B2 | 1/2011 | Rezai et al. |
| 7,890,182 B2 | 2/2011 | Parramon et al. |
| D638,439 S | 5/2011 | Cavanaugh et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,063,087 B2 | 11/2011 | Chow et al. |
| 8,100,815 B2 | 1/2012 | Balaker et al. |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,224,453 B2 | 7/2012 | De Ridder |
| 8,229,565 B2 | 7/2012 | Kim et al. |
| 8,238,666 B2 | 8/2012 | Besley et al. |
| 8,239,038 B2 | 8/2012 | Wolf, II |
| 8,260,436 B2 | 9/2012 | Gerber et al. |
| 8,265,770 B2 | 9/2012 | Toy et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,326,569 B2 | 12/2012 | Lee et al. |
| 8,332,029 B2 | 12/2012 | Glukhovsky et al. |
| 8,332,047 B2 | 12/2012 | Libbus et al. |
| 8,332,053 B1 | 12/2012 | Patterson et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| D677,674 S | 3/2013 | Rampson et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| D684,991 S | 6/2013 | Wenz et al. |
| D684,996 S | 6/2013 | Wenz et al. |
| 8,543,200 B2 | 9/2013 | Lane et al. |
| D691,154 S | 10/2013 | Talbot et al. |
| D691,172 S | 10/2013 | Wujcik et al. |
| 8,588,884 B2 | 11/2013 | Hegde et al. |
| D694,763 S | 12/2013 | Edwards et al. |
| 8,626,300 B2 | 1/2014 | Demarais et al. |
| 8,630,717 B2 | 1/2014 | Olson et al. |
| 8,700,145 B2 | 4/2014 | Kilgard et al. |
| 8,712,546 B2 | 4/2014 | Kim et al. |
| D705,241 S | 5/2014 | Chen et al. |
| D707,235 S | 6/2014 | Arnold et al. |
| 8,740,825 B2 | 6/2014 | Ehrenreich et al. |
| 8,750,957 B2 | 6/2014 | Tang et al. |
| RE45,030 E | 7/2014 | Stevenson et al. |
| 8,766,928 B2 | 7/2014 | Weeldreyer et al. |
| 8,768,472 B2 | 7/2014 | Fang et al. |
| 8,768,481 B2 | 7/2014 | Lane |
| 8,805,542 B2 | 8/2014 | Tai et al. |
| 8,836,368 B2 | 9/2014 | Afshar et al. |
| 8,847,548 B2 | 9/2014 | Kesler et al. |
| 8,849,410 B2 | 9/2014 | Walker et al. |
| 8,849,418 B2 | 9/2014 | Daglow |
| 8,897,870 B2 | 11/2014 | De Ridder |
| D721,722 S | 1/2015 | Lee |
| 8,957,549 B2 | 2/2015 | Kesler et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,192,768 B2 | 11/2015 | Yokoi et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| D750,664 S | 3/2016 | Chen et al. |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| D758,398 S | 6/2016 | Yu et al. |
| 9,358,384 B2 | 6/2016 | Dubuclet |
| D760,753 S | 7/2016 | Cheng et al. |
| 9,393,409 B2 | 7/2016 | Edgerton et al. |
| D763,273 S | 8/2016 | Hwang et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| D769,302 S | 10/2016 | Rodriguez |
| D770,468 S | 11/2016 | Carlson et al. |
| D770,470 S | 11/2016 | Jin |
| 9,520,887 B1 | 12/2016 | Zhuang et al. |
| D780,768 S | 3/2017 | Carlson et al. |
| 9,592,358 B2 | 3/2017 | Miller et al. |
| 9,592,385 B2 | 3/2017 | Kaula et al. |
| 9,597,517 B2 | 3/2017 | Moffitt |
| 9,610,442 B2 | 4/2017 | Yoo et al. |
| 9,639,982 B2 | 5/2017 | Craik et al. |
| 9,656,076 B2 | 5/2017 | Trier et al. |
| D794,667 S | 8/2017 | Havaldar et al. |
| 9,717,908 B2 | 8/2017 | Karunasiri |
| 9,724,513 B2 | 8/2017 | Lane et al. |
| 9,802,052 B2 | 10/2017 | Marnfeldt |
| 9,812,875 B2 | 11/2017 | Nejatali et al. |
| D806,717 S | 1/2018 | Bae et al. |
| 9,894,454 B2 | 2/2018 | Rao et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| D839,278 S | 1/2019 | Carlson et al. |

(56) References Cited

U.S. PATENT DOCUMENTS

| | | |
|---|---|---|
| D839,914 S | 2/2019 | Lee et al. |
| D841,017 S | 2/2019 | Bathla |
| D843,388 S | 3/2019 | Protzman et al. |
| 10,406,366 B2 | 9/2019 | Westlund et al. |
| 10,449,371 B2 | 10/2019 | Serrano Carmona |
| D874,491 S | 2/2020 | Kuo et al. |
| D874,507 S | 2/2020 | Martell et al. |
| D875,108 S | 2/2020 | Chitalia et al. |
| D875,752 S | 2/2020 | Nelson et al. |
| D877,753 S | 3/2020 | Chitalia et al. |
| 10,751,533 B2 | 8/2020 | Edgerton et al. |
| 10,758,732 B1 | 9/2020 | Heldman |
| 10,773,074 B2 | 9/2020 | Liu et al. |
| 10,799,701 B2 | 10/2020 | Lee |
| 10,806,927 B2 | 10/2020 | Edgerton et al. |
| 10,806,935 B2 | 10/2020 | Rao et al. |
| D904,437 S | 12/2020 | Chitalia et al. |
| 10,881,853 B2 | 1/2021 | Edgerton et al. |
| 10,898,719 B2 | 1/2021 | Pivonka et al. |
| D912,074 S | 3/2021 | Giannino et al. |
| D926,784 S | 8/2021 | Carlson et al. |
| 11,097,122 B2 | 8/2021 | Lu |
| 11,123,312 B2 | 9/2021 | Lu et al. |
| 11,129,983 B2 | 9/2021 | Lo et al. |
| D947,216 S | 3/2022 | Leininger |
| 11,266,850 B2 | 3/2022 | Prouza et al. |
| 11,298,533 B2 | 4/2022 | Edgerton et al. |
| D962,245 S | 8/2022 | Thompson et al. |
| 11,400,284 B2 | 8/2022 | Gerasimenko et al. |
| 11,491,336 B2 | 11/2022 | Scheltienne et al. |
| 11,511,116 B2 | 11/2022 | Wagner et al. |
| 11,515,733 B2 | 11/2022 | Babakhani et al. |
| 11,638,820 B2 | 5/2023 | Edgerton et al. |
| 11,691,015 B2 | 7/2023 | Minassian et al. |
| D1,008,290 S | 12/2023 | Stapfer |
| D1,008,291 S | 12/2023 | Stapfer |
| D1,010,666 S | 1/2024 | Cai et al. |
| 11,911,621 B2 | 2/2024 | Ganty et al. |
| 11,944,814 B2 | 4/2024 | Lo et al. |
| 11,957,910 B2 | 4/2024 | Edgerton et al. |
| 11,986,653 B2 | 5/2024 | Lo et al. |
| 11,992,684 B2 | 5/2024 | Minassian et al. |
| 12,018,135 B2 | 6/2024 | Scher et al. |
| 12,023,492 B2 | 7/2024 | Edgerton et al. |
| 12,076,301 B2 | 9/2024 | Lu et al. |
| D1,044,827 S | 10/2024 | Tabrizi et al. |
| 12,201,833 B2 | 1/2025 | Edgerton et al. |
| 12,268,878 B2 | 4/2025 | Phillips et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0050456 A1 | 5/2002 | Sheppard, Jr. et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0123672 A1 | 9/2002 | Christophersom et al. |
| 2002/0138512 A1 | 9/2002 | Buresh et al. |
| 2002/0173505 A1 | 11/2002 | Skogvall |
| 2002/0187260 A1 | 12/2002 | Sheppard, Jr. et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0093131 A1 | 5/2003 | Loeb et al. |
| 2003/0097166 A1 | 5/2003 | Krulevitch et al. |
| 2003/0100933 A1 | 5/2003 | Ayal et al. |
| 2003/0113725 A1 | 6/2003 | Small et al. |
| 2003/0114894 A1 | 6/2003 | Dar et al. |
| 2003/0114899 A1 | 6/2003 | Woods et al. |
| 2003/0135253 A1 | 7/2003 | Kokones et al. |
| 2003/0139422 A1 | 7/2003 | Teng |
| 2003/0145759 A1 | 8/2003 | Rodnunsky |
| 2003/0158583 A1 | 8/2003 | Burnett et al. |
| 2003/0199116 A1 | 10/2003 | Tai et al. |
| 2003/0200323 A1 | 10/2003 | Dold et al. |
| 2003/0208248 A1 | 11/2003 | Carter et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0087286 A1 | 5/2004 | Inoue et al. |
| 2004/0088015 A1 | 5/2004 | Casavant et al. |
| 2004/0111118 A1 | 6/2004 | Hill et al. |
| 2004/0111126 A1 | 6/2004 | Tanagho et al. |
| 2004/0121528 A1 | 6/2004 | Krulevitch et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0192082 A1 | 9/2004 | Wagner et al. |
| 2004/0192834 A1 | 9/2004 | Nakayoshi et al. |
| 2004/0243204 A1 | 12/2004 | Maghribi et al. |
| 2004/0267320 A1 | 12/2004 | Taylor et al. |
| 2005/0004622 A1 | 1/2005 | Cullen et al. |
| 2005/0043775 A1 | 2/2005 | John et al. |
| 2005/0061315 A1 | 3/2005 | Lee et al. |
| 2005/0070982 A1 | 3/2005 | Heruth et al. |
| 2005/0075662 A1 | 4/2005 | Pedersen et al. |
| 2005/0075669 A1 | 4/2005 | King |
| 2005/0075678 A1 | 4/2005 | Faul |
| 2005/0075693 A1 | 4/2005 | Toy et al. |
| 2005/0080460 A1 | 4/2005 | Wang et al. |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0203588 A1 | 9/2005 | King |
| 2005/0205961 A1 | 9/2005 | Doong |
| 2005/0209655 A1 | 9/2005 | Bradley et al. |
| 2005/0231186 A1 | 10/2005 | Saavedra Barrera et al. |
| 2005/0239612 A1 | 10/2005 | Keiser |
| 2005/0246004 A1 | 11/2005 | Cameron et al. |
| 2005/0253273 A1 | 11/2005 | Tai et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0007983 A1 | 1/2006 | Tai et al. |
| 2006/0015153 A1 | 1/2006 | Gliner et al. |
| 2006/0015470 A1 | 1/2006 | Lauer et al. |
| 2006/0016266 A1 | 1/2006 | Weise et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0047325 A1 | 3/2006 | Thimineur et al. |
| 2006/0082626 A1 | 4/2006 | Oikawa et al. |
| 2006/0089696 A1 | 4/2006 | Olsen et al. |
| 2006/0095088 A1 | 5/2006 | De Ridder |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189453 A1 | 8/2006 | Leblond |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0009968 A1 | 1/2007 | Cunningham et al. |
| 2007/0016097 A1 | 1/2007 | Farquhar et al. |
| 2007/0016266 A1 | 1/2007 | Paul, Jr. |

(56) References Cited

U.S. PATENT DOCUMENTS

| | | |
|---|---|---|
| 2007/0016268 A1 | 1/2007 | Carter et al. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055318 A1 | 3/2007 | Forsberg et al. |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0129769 A1 | 6/2007 | Bourget et al. |
| 2007/0142874 A1 | 6/2007 | John |
| 2007/0142878 A1 | 6/2007 | Krulevitch et al. |
| 2007/0150023 A1 | 6/2007 | Ignagni et al. |
| 2007/0150032 A1 | 6/2007 | Hiereth et al. |
| 2007/0150034 A1 | 6/2007 | Rooney et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0250119 A1 | 10/2007 | Tyler et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0282378 A1 | 12/2007 | Huang et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0092911 A1 | 4/2008 | Schulman et al. |
| 2008/0103579 A1 | 5/2008 | Gerber |
| 2008/0105185 A1 | 5/2008 | Kuhlman |
| 2008/0127031 A1 | 5/2008 | Olsson et al. |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183097 A1 | 7/2008 | Leyde et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0255582 A1 | 10/2008 | Harris |
| 2008/0269854 A1 | 10/2008 | Hegland et al. |
| 2008/0275129 A1 | 11/2008 | Lundstedt et al. |
| 2008/0279896 A1 | 11/2008 | Heinen et al. |
| 2008/0287268 A1 | 11/2008 | Hidler |
| 2008/0294211 A1 | 11/2008 | Moffitt |
| 2008/0294226 A1 | 11/2008 | Moffitt et al. |
| 2008/0318733 A1 | 12/2008 | Osler-Weppenaar |
| 2009/0005844 A1 | 1/2009 | Swoyer et al. |
| 2009/0012436 A1 | 1/2009 | Lanfermann et al. |
| 2009/0024186 A1 | 1/2009 | Brockway et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0227925 A1 | 9/2009 | McBean et al. |
| 2009/0229166 A1 | 9/2009 | Sawrie |
| 2009/0254151 A1 | 10/2009 | Anderson et al. |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2009/0312165 A1 | 12/2009 | Rempe |
| 2010/0004715 A1 | 1/2010 | Fahey |
| 2010/0006737 A1 | 1/2010 | Colombo et al. |
| 2010/0008782 A1 | 1/2010 | Danescu et al. |
| 2010/0010646 A1 | 1/2010 | Drew et al. |
| 2010/0016732 A1 | 1/2010 | Wells et al. |
| 2010/0023069 A1 | 1/2010 | Moffitt et al. |
| 2010/0023070 A1 | 1/2010 | Moffitt et al. |
| 2010/0023103 A1 | 1/2010 | Elborno |
| 2010/0029040 A1 | 2/2010 | Nomoto |
| 2010/0042193 A1 | 2/2010 | Slavin |
| 2010/0057177 A1 | 3/2010 | Moffitt et al. |
| 2010/0063568 A1 | 3/2010 | Staunton et al. |
| 2010/0070007 A1 | 3/2010 | Parker et al. |
| 2010/0070010 A1 | 3/2010 | Simpson |
| 2010/0087782 A1 | 4/2010 | Ghaffari et al. |
| 2010/0094800 A1 | 4/2010 | Sharp |
| 2010/0114205 A1 | 5/2010 | Donofrio et al. |
| 2010/0114239 A1 | 5/2010 | McDonald, III |
| 2010/0116526 A1 | 5/2010 | Arora et al. |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0137943 A1 | 6/2010 | Zhu |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0179562 A1 | 7/2010 | Linker et al. |
| 2010/0185253 A1 | 7/2010 | Dimarco et al. |
| 2010/0191307 A1 | 7/2010 | Fang et al. |
| 2010/0198298 A1 | 8/2010 | Glukhovsky et al. |
| 2010/0217355 A1 | 8/2010 | Tass et al. |
| 2010/0217418 A1 | 8/2010 | Fontanot |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0279606 A1 | 11/2010 | Hillan et al. |
| 2010/0280570 A1 | 11/2010 | Sturm et al. |
| 2010/0298905 A1 | 11/2010 | Simon |
| 2010/0298910 A1 | 11/2010 | Carbunaru et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0324699 A1 | 12/2010 | Herr et al. |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |

(56) References Cited

U.S. PATENT DOCUMENTS

| | | |
|---|---|---|
| 2011/0034912 A1 | 2/2011 | de Graff et al. |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0060461 A1 | 3/2011 | Velliste et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0112611 A1 | 5/2011 | Aghassian |
| 2011/0118815 A1 | 5/2011 | Kuzma et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0201944 A1 | 8/2011 | Higgins et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224755 A1 | 9/2011 | Arle et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0230747 A1 | 9/2011 | Rogers et al. |
| 2011/0230808 A1 | 9/2011 | Lisowski |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |
| 2011/0260126 A1 | 10/2011 | Willis |
| 2011/0270360 A1 | 11/2011 | Harris et al. |
| 2011/0276107 A1 | 11/2011 | Simon et al. |
| 2011/0288609 A1 | 11/2011 | Tehrani et al. |
| 2011/0295100 A1 | 12/2011 | Hegde et al. |
| 2012/0006793 A1 | 1/2012 | Swanson |
| 2012/0011222 A1 | 1/2012 | Yasukawa et al. |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0016453 A1 | 1/2012 | Feler et al. |
| 2012/0018249 A1 | 1/2012 | Mehr |
| 2012/0022371 A1 | 1/2012 | Summerton |
| 2012/0022551 A1 | 1/2012 | Staunton et al. |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0053645 A1 | 3/2012 | Ayanoor-Vitikkate et al. |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0116478 A1 | 5/2012 | Buhlmann et al. |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0143281 A1 | 6/2012 | Birkill et al. |
| 2012/0161531 A1 | 6/2012 | Kim |
| 2012/0161721 A1 | 6/2012 | Neethimanickam |
| 2012/0165899 A1 | 6/2012 | Gliner |
| 2012/0168397 A1 | 7/2012 | Lim et al. |
| 2012/0172222 A1 | 7/2012 | Artigas Puerto |
| 2012/0172246 A1 | 7/2012 | Nguyen et al. |
| 2012/0172510 A1 | 7/2012 | Esseghir et al. |
| 2012/0172946 A1 | 7/2012 | Alataris et al. |
| 2012/0179222 A1 | 7/2012 | Jaax et al. |
| 2012/0185020 A1 | 7/2012 | Simon |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0203246 A1 | 8/2012 | Staunton et al. |
| 2012/0221073 A1 | 8/2012 | Southwell et al. |
| 2012/0232615 A1 | 9/2012 | Barolat et al. |
| 2012/0252380 A1 | 10/2012 | Kawakita |
| 2012/0252874 A1 | 10/2012 | Feinstein et al. |
| 2012/0259380 A1 | 10/2012 | Pyles |
| 2012/0265269 A1 | 10/2012 | Lui |
| 2012/0271315 A1 | 10/2012 | Pianca et al. |
| 2012/0271372 A1 | 10/2012 | Osorio |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0006322 A1 | 1/2013 | Tai |
| 2013/0006793 A1 | 1/2013 | O'Sullivan et al. |
| 2013/0012853 A1 | 1/2013 | Brown |
| 2013/0013041 A1 | 1/2013 | Glukhovsky et al. |
| 2013/0023972 A1 | 1/2013 | Kuzma et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0032508 A1 | 2/2013 | Azuma |
| 2013/0035745 A1 | 2/2013 | Ahmed et al. |
| 2013/0041235 A1 | 2/2013 | Rogers et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0066411 A1 | 3/2013 | Thacker et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116604 A1 | 5/2013 | Morilla et al. |
| 2013/0116751 A1 | 5/2013 | Moffitt et al. |
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0150915 A1 | 6/2013 | Kane et al. |
| 2013/0154373 A1 | 6/2013 | Lisuwandi et al. |
| 2013/0158444 A1 | 6/2013 | Herr et al. |
| 2013/0165991 A1 | 6/2013 | Kim et al. |
| 2013/0190143 A1 | 7/2013 | Greenhill et al. |
| 2013/0197408 A1 | 8/2013 | Goldfarb et al. |
| 2013/0204324 A1 | 8/2013 | Thacker et al. |
| 2013/0211477 A1 | 8/2013 | Cullen et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268020 A1 | 10/2013 | Rosenberg et al. |
| 2013/0268021 A1 | 10/2013 | Moffitt |
| 2013/0268041 A1 | 10/2013 | Schulte et al. |
| 2013/0281890 A1 | 10/2013 | Mishelevich |

(56) References Cited

U.S. PATENT DOCUMENTS

| | | |
|---|---|---|
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2013/0325081 A1 | 12/2013 | Karst et al. |
| 2013/0325083 A1 | 12/2013 | Bharmi et al. |
| 2013/0345780 A1 | 12/2013 | Tabada et al. |
| 2014/0005753 A1 | 1/2014 | Carbunaru |
| 2014/0031893 A1 | 1/2014 | Walker et al. |
| 2014/0031895 A1 | 1/2014 | Rahimi et al. |
| 2014/0046407 A1 | 2/2014 | Ben-Ezra et al. |
| 2014/0053401 A1 | 2/2014 | Kuzma et al. |
| 2014/0058292 A1 | 2/2014 | Alford et al. |
| 2014/0058490 A1 | 2/2014 | DiMarco |
| 2014/0059499 A1 | 2/2014 | Kim et al. |
| 2014/0066950 A1 | 3/2014 | MacDonald et al. |
| 2014/0067007 A1 | 3/2014 | Drees et al. |
| 2014/0067013 A1* | 3/2014 | Kaula ............... A61N 1/36142 607/59 |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0081345 A1 | 3/2014 | Hershey |
| 2014/0087922 A1 | 3/2014 | Bayerlein et al. |
| 2014/0088674 A1 | 3/2014 | Bradley |
| 2014/0100491 A1 | 4/2014 | Hu et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0114385 A1 | 4/2014 | Nijhuis et al. |
| 2014/0124713 A1 | 5/2014 | Majumdar et al. |
| 2014/0142652 A1 | 5/2014 | Francois et al. |
| 2014/0163640 A1 | 6/2014 | Edgerton et al. |
| 2014/0171961 A1 | 6/2014 | Lacey et al. |
| 2014/0172045 A1 | 6/2014 | Yip et al. |
| 2014/0172055 A1 | 6/2014 | Venancio |
| 2014/0180361 A1 | 6/2014 | Burdick et al. |
| 2014/0201905 A1 | 7/2014 | Glukhovsky |
| 2014/0213842 A1 | 7/2014 | Simon et al. |
| 2014/0213844 A1 | 7/2014 | Pilla et al. |
| 2014/0228905 A1 | 8/2014 | Bolea |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303685 A1 | 10/2014 | Rosenberg et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon de Lima et al. |
| 2014/0339909 A1 | 11/2014 | Sugawara |
| 2014/0343623 A1 | 11/2014 | Alves et al. |
| 2014/0357936 A1 | 12/2014 | Simon et al. |
| 2014/0359521 A1 | 12/2014 | Lin et al. |
| 2014/0371830 A1 | 12/2014 | Howard et al. |
| 2015/0005167 A1 | 1/2015 | Jung et al. |
| 2015/0005840 A1 | 1/2015 | Pal et al. |
| 2015/0012061 A1 | 1/2015 | Chen |
| 2015/0022143 A1 | 1/2015 | Kim |
| 2015/0032187 A1 | 1/2015 | Ranu et al. |
| 2015/0051674 A1 | 2/2015 | Barner et al. |
| 2015/0057717 A1 | 2/2015 | Wu et al. |
| 2015/0065559 A1 | 3/2015 | Feinstein et al. |
| 2015/0066111 A1 | 3/2015 | Blum et al. |
| 2015/0074997 A1 | 3/2015 | Kuzma et al. |
| 2015/0088212 A1 | 3/2015 | De Ridder |
| 2015/0094734 A1 | 4/2015 | Staunton et al. |
| 2015/0094791 A1 | 4/2015 | Edgell et al. |
| 2015/0120634 A1 | 4/2015 | Tateno |
| 2015/0126120 A1 | 5/2015 | Chen |
| 2015/0148878 A1 | 5/2015 | Yoo et al. |
| 2015/0151114 A1 | 6/2015 | Black et al. |
| 2015/0151126 A1 | 6/2015 | Kishawi et al. |
| 2015/0165226 A1 | 6/2015 | Simon et al. |
| 2015/0174411 A1 | 6/2015 | Ranu |
| 2015/0182784 A1 | 7/2015 | Barriskill et al. |
| 2015/0188592 A1 | 7/2015 | Solondz |
| 2015/0190200 A1 | 7/2015 | Courtine et al. |
| 2015/0190634 A1 | 7/2015 | Rezai et al. |
| 2015/0196231 A1 | 7/2015 | Ziaie et al. |
| 2015/0196241 A1 | 7/2015 | Yekutieli |
| 2015/0200561 A1 | 7/2015 | Lee et al. |
| 2015/0217120 A1 | 8/2015 | Nandra et al. |
| 2015/0224326 A1 | 8/2015 | Toth et al. |
| 2015/0231326 A1 | 8/2015 | Milner et al. |
| 2015/0231396 A1 | 8/2015 | Burdick et al. |
| 2015/0246216 A1 | 9/2015 | Barker |
| 2015/0265830 A1 | 9/2015 | Simon et al. |
| 2015/0268845 A1 | 9/2015 | Endo |
| 2015/0320632 A1 | 11/2015 | Vallery et al. |
| 2015/0328462 A1 | 11/2015 | Griffith |
| 2015/0343199 A1 | 12/2015 | Wechter et al. |
| 2015/0343205 A1 | 12/2015 | Howard et al. |
| 2016/0001096 A1 | 1/2016 | Mishelevich |
| 2016/0005538 A1 | 1/2016 | Koyanagi et al. |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0067477 A1 | 3/2016 | Dubuclet |
| 2016/0074663 A1 | 3/2016 | De Ridder |
| 2016/0082261 A1 | 3/2016 | Moffitt et al. |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0136477 A1 | 5/2016 | Bucher et al. |
| 2016/0143588 A1 | 5/2016 | Hoitink et al. |
| 2016/0144167 A1 | 5/2016 | Bakker et al. |
| 2016/0144184 A1 | 5/2016 | Marnfeldt |
| 2016/0157389 A1 | 6/2016 | Hwang |
| 2016/0166828 A1 | 6/2016 | Yu |
| 2016/0175586 A1 | 6/2016 | Edgerton et al. |
| 2016/0197488 A1 | 7/2016 | Hada et al. |
| 2016/0213918 A1 | 7/2016 | Howard et al. |
| 2016/0220813 A1 | 8/2016 | Edgerton et al. |
| 2016/0228706 A1 | 8/2016 | Hershey et al. |
| 2016/0235977 A1 | 8/2016 | Lu et al. |
| 2016/0250461 A1 | 9/2016 | Dubuclet |
| 2016/0263376 A1 | 9/2016 | Yoo et al. |
| 2016/0271413 A1 | 9/2016 | Vallejo et al. |
| 2016/0279418 A1 | 9/2016 | Courtine et al. |
| 2016/0279429 A1 | 9/2016 | Hershey et al. |
| 2016/0310739 A1 | 10/2016 | Burdick et al. |
| 2016/0339239 A1 | 11/2016 | Yoo et al. |
| 2016/0367827 A1 | 12/2016 | Tahmasian |
| 2017/0007320 A1 | 1/2017 | Levin et al. |
| 2017/0007831 A1 | 1/2017 | Edgerton et al. |
| 2017/0014620 A9 | 1/2017 | Staunton et al. |
| 2017/0014622 A1 | 1/2017 | Bozung et al. |
| 2017/0065814 A1 | 3/2017 | Howard et al. |
| 2017/0079598 A1 | 3/2017 | Stolen et al. |
| 2017/0098951 A1 | 4/2017 | Olgun et al. |
| 2017/0098962 A1 | 4/2017 | Desrosiers |
| 2017/0118722 A1 | 4/2017 | Hong et al. |
| 2017/0128729 A1 | 5/2017 | Netoff et al. |
| 2017/0156662 A1 | 6/2017 | Goodall et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0189686 A1 | 7/2017 | Steinke et al. |

(56) References Cited

U.S. PATENT DOCUMENTS

| | | |
|---|---|---|
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0291023 A1 | 10/2017 | Kuzma et al. |
| 2017/0296837 A1 | 10/2017 | Jin |
| 2017/0338570 A1 | 11/2017 | Myers |
| 2017/0348523 A1 | 12/2017 | Rubehn et al. |
| 2017/0348532 A1 | 12/2017 | Moffitt et al. |
| 2017/0354819 A1 | 12/2017 | Bloch et al. |
| 2017/0361093 A1 | 12/2017 | Yoo |
| 2017/0361115 A1 | 12/2017 | Aghassian et al. |
| 2018/0008826 A1 | 1/2018 | Dimarco |
| 2018/0028812 A1 | 2/2018 | Vallejo et al. |
| 2018/0056078 A1 | 3/2018 | Kashyap et al. |
| 2018/0083473 A1 | 3/2018 | Menegoli et al. |
| 2018/0085583 A1 | 3/2018 | Zhang et al. |
| 2018/0093093 A1 | 4/2018 | Courtine et al. |
| 2018/0104479 A1 | 4/2018 | Grill et al. |
| 2018/0110992 A1 | 4/2018 | Parramon et al. |
| 2018/0117334 A1 | 5/2018 | Jung |
| 2018/0125416 A1 | 5/2018 | Schwarz et al. |
| 2018/0125419 A1 | 5/2018 | Yun et al. |
| 2018/0126154 A1 | 5/2018 | Dubuclet |
| 2018/0126155 A1 | 5/2018 | Mclaughlin et al. |
| 2018/0133480 A1 | 5/2018 | Annoni et al. |
| 2018/0133481 A1 | 5/2018 | Von Zitzewitz et al. |
| 2018/0153474 A1 | 6/2018 | Aeschlimann et al. |
| 2018/0178008 A1 | 6/2018 | Bouton et al. |
| 2018/0185632 A1 | 7/2018 | Staunton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0214694 A1 | 8/2018 | Parramon |
| 2018/0221651 A1 | 8/2018 | Chang et al. |
| 2018/0228421 A1 | 8/2018 | Saab |
| 2018/0229037 A1 | 8/2018 | Edgerton et al. |
| 2018/0229038 A1 | 8/2018 | Burdick et al. |
| 2018/0236240 A1 | 8/2018 | Harkema et al. |
| 2018/0256906 A1 | 9/2018 | Pivonka et al. |
| 2018/0272125 A1 | 9/2018 | Sandhu |
| 2018/0272132 A1 | 9/2018 | Subbaroyan et al. |
| 2018/0280693 A1 | 10/2018 | Edgerton et al. |
| 2018/0280706 A1 | 10/2018 | Maile et al. |
| 2018/0289971 A1 | 10/2018 | Yeh et al. |
| 2018/0294547 A1 | 10/2018 | Park et al. |
| 2018/0318576 A1 | 11/2018 | Bozung et al. |
| 2018/0337547 A1 | 11/2018 | Menegoli et al. |
| 2018/0353755 A1 | 12/2018 | Edgerton et al. |
| 2018/0361146 A1 | 12/2018 | Gerasimenko et al. |
| 2018/0367187 A1 | 12/2018 | McFarthing |
| 2018/0369574 A1 | 12/2018 | Dubuclet et al. |
| 2018/0369575 A1 | 12/2018 | Dubuclet et al. |
| 2018/0369576 A1 | 12/2018 | Dubuclet et al. |
| 2019/0001122 A1 | 1/2019 | Ganty et al. |
| 2019/0001139 A1 | 1/2019 | Mishra et al. |
| 2019/0009094 A1 | 1/2019 | Zhang et al. |
| 2019/0017983 A1 | 1/2019 | Smith |
| 2019/0022371 A1 | 1/2019 | Chang et al. |
| 2019/0027257 A1 | 1/2019 | Ghogawala |
| 2019/0033622 A1 | 1/2019 | Olgun et al. |
| 2019/0160294 A1 | 5/2019 | Peterson et al. |
| 2019/0167980 A1 | 6/2019 | Peterson |
| 2019/0167987 A1 | 6/2019 | Lu et al. |
| 2019/0192852 A1 | 6/2019 | De Ridder |
| 2019/0192864 A1 | 6/2019 | Koop et al. |
| 2019/0240468 A1 | 8/2019 | Yun et al. |
| 2019/0247650 A1 | 8/2019 | Tran |
| 2019/0262609 A1 | 8/2019 | Brill et al. |
| 2019/0269917 A1 | 9/2019 | Courtine et al. |
| 2019/0299006 A1 | 10/2019 | Marnfeldt |
| 2019/0321639 A1 | 10/2019 | Rao et al. |
| 2019/0336760 A1 | 11/2019 | Shah |
| 2019/0344070 A1 | 11/2019 | Molnar et al. |
| 2019/0344075 A1 | 11/2019 | Bloch et al. |
| 2019/0358454 A1 | 11/2019 | Lin et al. |
| 2019/0374776 A1 | 12/2019 | Mishra et al. |
| 2019/0374777 A1 | 12/2019 | Burdick et al. |
| 2019/0381313 A1 | 12/2019 | Lu |
| 2019/0381328 A1 | 12/2019 | Wechter et al. |
| 2019/0381382 A1 | 12/2019 | Wu |
| 2020/0009385 A1 | 1/2020 | Shah |
| 2020/0060602 A1 | 2/2020 | Wagner et al. |
| 2020/0061378 A1 | 2/2020 | Ganguly et al. |
| 2020/0086116 A1 | 3/2020 | Formento et al. |
| 2020/0121544 A1 | 4/2020 | George et al. |
| 2020/0139126 A1 | 5/2020 | Napadow et al. |
| 2020/0144846 A1 | 5/2020 | Shin |
| 2020/0147382 A1 | 5/2020 | Caban et al. |
| 2020/0155019 A1 | 5/2020 | Esteller et al. |
| 2020/0155865 A1 | 5/2020 | Lu |
| 2020/0228901 A1 | 7/2020 | Baek |
| 2020/0398068 A1 | 12/2020 | Agnihotri et al. |
| 2021/0069052 A1 | 3/2021 | Burke |
| 2021/0093865 A1 | 4/2021 | Vallejo et al. |
| 2021/0121692 A1 | 4/2021 | Edgerton et al. |
| 2021/0153942 A1 | 5/2021 | Scheltienne et al. |
| 2021/0154481 A1 | 5/2021 | Scheltienne et al. |
| 2021/0170177 A1 | 6/2021 | Minassian et al. |
| 2021/0170178 A1 | 6/2021 | Wagner et al. |
| 2021/0187278 A1 | 6/2021 | Lu |
| 2021/0213292 A1 | 7/2021 | Minassian et al. |
| 2021/0236837 A1 | 8/2021 | Lu |
| 2021/0275810 A1 | 9/2021 | Caban |
| 2021/0290955 A1 | 9/2021 | Brouns et al. |
| 2021/0299441 A1 | 9/2021 | Edgerton et al. |
| 2021/0378991 A1 | 12/2021 | Lu |
| 2021/0402186 A1 | 12/2021 | Edgerton et al. |
| 2022/0016420 A1 | 1/2022 | Lo et al. |
| 2022/0111208 A1 | 4/2022 | Phillips et al. |
| 2022/0125374 A1 | 4/2022 | Courtine et al. |
| 2022/0134108 A1 | 5/2022 | Dinsmoor et al. |
| 2022/0143407 A1 | 5/2022 | Zhuang et al. |
| 2022/0161042 A1 | 5/2022 | Lu |
| 2022/0176130 A1 | 6/2022 | Wu et al. |
| 2022/0184386 A1 | 6/2022 | Courtine et al. |
| 2022/0233848 A1 | 7/2022 | Gad et al. |
| 2022/0313993 A1 | 10/2022 | Gerasimenko et al. |
| 2022/0409899 A1 | 12/2022 | Ganty et al. |
| 2023/0045403 A1 | 2/2023 | Robison et al. |
| 2023/0053053 A1 | 2/2023 | Delattre et al. |
| 2023/0186201 A1 | 6/2023 | Cella et al. |
| 2023/0281527 A1 | 9/2023 | Cella et al. |
| 2024/0001116 A1 | 1/2024 | Edgerton et al. |
| 2024/0050746 A1 | 2/2024 | Angeli et al. |
| 2024/0335666 A1 | 10/2024 | Murphy |
| 2024/0374541 A1 | 11/2024 | Lu et al. |
| 2024/0424291 A1 | 12/2024 | Ganty et al. |
| 2024/0424302 A1 | 12/2024 | Dumeny |
| 2025/0025689 A1 | 1/2025 | Lo et al. |
| 2025/0032799 A1 | 1/2025 | Weijand et al. |

FOREIGN PATENT DOCUMENTS

| | | |
|---|---|---|
| CA | 2856202 A1 | 5/2013 |
| CA | 2864473 A1 | 5/2013 |
| CA | 3034123 A1 | 2/2018 |
| CA | 2823592 A1 | 11/2021 |
| CN | 101227940 A | 7/2008 |
| CN | 101822223 A | 8/2013 |
| CN | 103263727 A | 8/2013 |
| CN | 104307098 A | 1/2015 |
| DE | 3830429 A1 | 3/1990 |
| DE | 2020007015508 U1 | 3/2008 |
| EP | 0034145 A1 | 8/1981 |
| EP | 0236976 A1 | 9/1987 |
| EP | 0630987 A1 | 12/1994 |
| EP | 1127907 A2 | 8/2001 |
| EP | 1303332 A1 | 4/2003 |
| EP | 1303332 B1 | 4/2003 |
| EP | 1575665 A1 | 9/2005 |
| EP | 1675648 A1 | 7/2006 |
| EP | 1680182 A1 | 7/2006 |
| EP | 2130326 A1 | 12/2009 |

(56) References Cited

FOREIGN PATENT DOCUMENTS

| | | | |
|---|---|---|---|
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2243510 A2 | 10/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2665514 A2 | 11/2013 |
| EP | 2688642 A2 | 1/2014 |
| EP | 2810689 A1 | 12/2014 |
| EP | 2810690 A1 | 12/2014 |
| EP | 2868323 A1 | 5/2015 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3269424 A1 | 1/2018 |
| EP | 3323468 A1 | 5/2018 |
| EP | 3328481 A1 | 6/2018 |
| EP | 3381506 A1 | 10/2018 |
| EP | 3421081 A1 | 1/2019 |
| EP | 3495019 A1 | 6/2019 |
| EP | 3527258 A1 | 8/2019 |
| EP | 3969100 B1 | 7/2023 |
| JP | H0326620 A | 2/1991 |
| JP | 3184145 B2 | 7/2001 |
| JP | 2002517283 A | 6/2002 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2009512516 A | 3/2009 |
| JP | 2011502586 A | 1/2011 |
| JP | 2011504112 A | 2/2011 |
| JP | 2012515060 A | 7/2012 |
| JP | 2013508119 A | 3/2013 |
| JP | 2014513562 A | 6/2014 |
| JP | 2014514043 A | 6/2014 |
| JP | 2016506255 A | 3/2016 |
| JP | 6132856 B2 | 5/2017 |
| JP | 2017104685 A | 6/2017 |
| JP | 2017523868 A1 | 8/2017 |
| JP | 2017525509 A | 9/2017 |
| JP | 2018524113 A | 8/2018 |
| KR | 101573840 B1 | 12/2015 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2193441 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | 8100458 A1 | 2/1981 |
| WO | WO 1994009808 A1 | 5/1994 |
| WO | WO 1997047357 A1 | 12/1997 |
| WO | WO 199908749 A1 | 2/1999 |
| WO | WO 200019912 A1 | 4/2000 |
| WO | WO 2002/009808 A1 | 2/2002 |
| WO | WO 2002034331 A2 | 5/2002 |
| WO | WO 2002092165 A1 | 11/2002 |
| WO | WO 2003005887 A2 | 1/2003 |
| WO | WO 2003026735 A2 | 4/2003 |
| WO | WO 2003092795 A1 | 11/2003 |
| WO | WO 2003094749 A1 | 11/2003 |
| WO | WO 2004087116 A2 | 10/2004 |
| WO | WO 2005002663 A2 | 1/2005 |
| WO | WO 2005051306 A2 | 6/2005 |
| WO | WO 2005065768 A1 | 7/2005 |
| WO | WO 2005087307 A2 | 9/2005 |
| WO | WO 2006026850 A1 | 3/2006 |
| WO | WO 2006/135751 A2 | 12/2006 |
| WO | WO 2006138069 A1 | 12/2006 |
| WO | 2007007057 A1 | 1/2007 |
| WO | WO 2007007058 A1 | 1/2007 |
| WO | WO 2007012114 A1 | 2/2007 |
| WO | WO 2007047852 A1 | 4/2007 |
| WO | WO 2007057508 A2 | 5/2007 |
| WO | WO 2007081764 A2 | 7/2007 |
| WO | WO 2007107831 A2 | 9/2007 |
| WO | WO 2008070807 A3 | 6/2008 |
| WO | WO 2008075294 A1 | 6/2008 |
| WO | WO 2008092785 A1 | 8/2008 |
| WO | WO 2008109862 A2 | 9/2008 |
| WO | WO 2008121891 A1 | 10/2008 |
| WO | WO 2009042217 A1 | 4/2009 |
| WO | WO 2009111142 A2 | 9/2009 |
| WO | WO 2010021977 A1 | 2/2010 |
| WO | WO 2010055421 A1 | 5/2010 |
| WO | 2010083308 A1 | 7/2010 |
| WO | WO 2010114998 A1 | 10/2010 |
| WO | WO 2010124128 A1 | 10/2010 |
| WO | WO 2011005607 A1 | 1/2011 |
| WO | WO 2011008459 A2 | 1/2011 |
| WO | WO 2011136875 A1 | 11/2011 |
| WO | WO 2012075195 A1 | 6/2012 |
| WO | WO 2012080964 A1 | 6/2012 |
| WO | WO 2012094346 A2 | 7/2012 |
| WO | WO 2012100260 A2 | 7/2012 |
| WO | WO 2012103519 A2 | 8/2012 |
| WO | WO 2012/129574 A3 | 9/2012 |
| WO | WO 2012129574 A2 | 9/2012 |
| WO | 2013049658 A1 | 4/2013 |
| WO | WO 2013069004 A1 | 5/2013 |
| WO | WO 2013071307 A1 | 5/2013 |
| WO | WO 2013071309 A1 | 5/2013 |
| WO | WO 2013117750 A1 | 8/2013 |
| WO | WO 2013152124 A1 | 10/2013 |
| WO | WO 2013179230 A1 | 12/2013 |
| WO | WO 2013188965 A1 | 12/2013 |
| WO | WO 2014005075 A1 | 1/2014 |
| WO | WO 2014031142 A1 | 2/2014 |
| WO | WO 2014089299 A2 | 6/2014 |
| WO | WO 2014144785 A1 | 9/2014 |
| WO | WO 2014149895 A1 | 9/2014 |
| WO | WO 2014205356 A2 | 12/2014 |
| WO | WO 2014209877 A1 | 12/2014 |
| WO | WO 2015000800 A1 | 1/2015 |
| WO | WO 2015048563 A2 | 4/2015 |
| WO | WO 2015063127 A1 | 5/2015 |
| WO | WO 2015106286 A1 | 7/2015 |
| WO | WO 2015172894 A1 | 11/2015 |
| WO | WO 2016005367 A1 | 1/2016 |
| WO | WO 2016029159 A2 | 2/2016 |
| WO | WO 20160025913 A1 | 2/2016 |
| WO | WO 2016033369 A1 | 3/2016 |
| WO | WO 2016033372 A1 | 3/2016 |
| WO | WO 2016064761 A1 | 4/2016 |
| WO | WO 2016110804 A1 | 7/2016 |
| WO | WO 2016112398 A1 | 7/2016 |
| WO | WO 2016172239 A1 | 10/2016 |

(56) References Cited

FOREIGN PATENT DOCUMENTS

| WO | WO 2017011410 A1 | 1/2017 |
|---|---|---|
| WO | WO 20170055661 A1 | 1/2017 |
| WO | WO 2017024276 A1 | 2/2017 |
| WO | WO 2017035512 A1 | 3/2017 |
| WO | WO 2017044904 A1 | 3/2017 |
| WO | WO 2017058913 A1 | 4/2017 |
| WO | WO 2017062508 A1 | 4/2017 |
| WO | WO 2017117450 A1 | 7/2017 |
| WO | WO 2017146659 A1 | 8/2017 |
| WO | WO 2017188965 A1 | 11/2017 |
| WO | WO 2018033591 A2 | 2/2018 |
| WO | WO 2018039296 A2 | 3/2018 |
| WO | WO 2018039458 A1 | 3/2018 |
| WO | WO 2018/063879 | 4/2018 |
| WO | WO 2018093765 A1 | 5/2018 |
| WO | WO 2018106843 A1 | 6/2018 |
| WO | WO 2018148844 A1 | 8/2018 |
| WO | WO 2018160531 A1 | 8/2018 |
| WO | WO 2018217791 A1 | 11/2018 |
| WO | WO 2012050200 A1 | 4/2019 |
| WO | WO 2019211314 A1 | 11/2019 |
| WO | WO 2020028088 A1 | 2/2020 |
| WO | WO 2020041502 A1 | 2/2020 |
| WO | WO 2020416331 A1 | 2/2020 |
| WO | WO 2020236946 A1 | 11/2020 |
| WO | D215131-0001 | 7/2022 |

OTHER PUBLICATIONS

Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.
Angeli, C. et al., "Altering spinal cord excitability enables voluntary movements after chronic complete paralysis in humans," Brain, vol. 137, No. 5, May 2014, Available Online Apr. 8, 2014, 16 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Azimi, J. et al., "Batch Active Learning via Coordinated Matching", In Proceedings of the 29th International Conference on Machine Learning, (2012), 8 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group Ia Synaptic Input to Fast and Slow Twitch Motor Units of Cat Triceps Surae", The Journal of Physiology, vol. 196, vol. 3, (Jun. 1, 1968), 26 pages.
Cai, L. et al., "Implications of Assist-as-Needed Robotic Step Training after a Complete Spinal Cord Injury on Intrinsic Strategies of Motor Learning", The Journal of Neuroscience, vol. 26, No. 41, (Oct. 11, 2006), 5 pages.
Capogrosso, M. et al., A Computational Model for Epidural Electrical Stimulation of Spinal Sensorimotor Circuits, Journal of Neuroscience, vol. 33, No. 49, Dec. 4, 2013, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Courtine, G. et al., "Transformation of nonfunctional spinal circuits into functional states after the loss of brain input," Nature Neuroscience, vol. 12, No. 10, Published Online Sep. 20, 2009, (Oct. 2009), 12 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Dani, V. et al., "Stochastic Linear Optimization Under Bandit Feedback", In Proceedings of the 21st Annual Conference on Learning Theory (COLT), (2008), 15 pages.
Danner, S. M. et al., "Body Position Influences Which neural structures are recruited by lumbar transcutaneous spinal cord stimulation", PLoS ONE, vol. 11, No. 1, (2016), 13 pages.
Danner, S. et al., "Human spinal locomotor control is based on flexibly organized burst generators," Brain, vol. 138, No. 3, Available Online Jan. 12, 2015, Mar. 2015, 12 pages.
Dimitrijevic, M. M. et al., "Evidence for a Spinal Central Pattern Generator in Humans", Annals New York Academy Sciences, vol. 860, (1998), pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004).
Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Training Locomotor Networks," Brain Research Reviews, vol. 57, Published Online Sep. 16, 2007, (Jan. 2008), 25 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.

(56) References Cited

OTHER PUBLICATIONS

European Search Report and Written Opinion in counterpart European Patent Application No. 19211738.0 dated May 27, 2020, Retrieved Mar. 12, 2021, (6 pages).
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.
Ganley, K. J. et al., "Epidural Spinal Cord Stimulation Improves Locomotor Performance in Low Asia C, Wheelchair-Dependent, Spinal Cord-Injured Individuals: Insights from Metabolic Response", Top. Spinal Cord Inj. Rehabil, vol. 11, No. 2, (2005), pp. 60-63.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harrison, P. et al., "Individual Excitatory Post-Synaptic Potentials Due to Muscle Spindle Ia Afferents in Cat Triceps Surae Motoneurones," The Journal of Physiology, vol. 312, No. 1, (Mar. 1981), pp. 455-470.
Harkema, S. et al., "Human Lumbosacral Spinal Cord Interprets Loading During Stepping," Journal of Neurophysiology, vol. 77, No. 2, (Feb. 1, 1997), 15 pages.
Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Hennig, P. et al., "Entropy search for information-efficient global optimization" Journal of Machine Learning Research (JMLR), vol. 13, (Jun. 2012), pp. 1809-1837.
Herman, R. et al., "Spinal cord stimulation facilitates functional walking in a chronic, incomplete spinal cord injured," Spinal Cord, vol. 40, No. 2, (2002), 4 pages.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, K. E. et al., "Computer Simulation of the Responses of Human Motoneurons to Composite 1A Epsps: Effects of Background Firing Rate," The Journal of Physiology, vol. 77, No. 1, (1997), 16 pages.
Jones, D. R. et al., "Efficient Global Optimization of Expensive Black-Box Functions", Journal of Global Optimization, vol. 13, (1998), pp. 455-492.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Las Vegas, Nevada, (Sep. 9, 1998), 6 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krause, A. et al. "Contextual Gaussian Process Bandit Optimization", In Advances in Neural Information Processing Systems (NIPS), (2011), 9 pages.
Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.
Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.

(56) References Cited

OTHER PUBLICATIONS

Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Liu, J. et al., "Stimulation of the Parapyramidal Region of the Neonatal Rat Brain Stem Produces Locomotor-Like Activity Involving Spinal 5-HT7 and 5-HT2A Receptors", Journal of Neurophysiology, vol. 94, No. 2, Published Online May 4, 2005, (Aug. 1, 2005), 13 pages.
Lizotte, D. et al., "Automatic gait optimization with Gaussian process regression", In IJCAI, (2007), pp. 944-949.
Lovely, R. et al., "Effects of Training on the Recovery of Full-Weight-Bearing Stepping in the Adult Spinal Cat," Experimental Neurology, vol. 92, No. 2, (May 1986), 15 pages.
Lozano, A. et al., "Probing and Regulating Dysfunctional Circuits Using Deep Brain Stimulation," Neuron, vol. 77, No. 3, (Feb. 6, 2013), 19 pages.
McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.
Minassian, K. et al., "Peripheral and Central Afferent Input to the Lumbar Cord", Biocybernetics and Biomedical Engineering, vol. 25, No. 3, (2005), pp. 11-29.
Minassian, K. et al., "Human lumbar cord circuitries can be activated by extrinsic tonic input to generate locomotor-like activity", Human Movement Science, vol. 26, No. 2, (2007), pp. 275-295.
Minassian, K. et al., "Posterior root-muscle reflex", Second Congress International Society of Intraoperative Neurophysiology (ISIN), Dubrovnik, Croatia, (2009), pp. 77-80.
Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.
Minassian, K. et al., "Neuromodulation of lower limb motor control in restorative neurology", Clinical Neurology and Neurosurgery, vol. 114, (2012), pp. 489-497.
Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.
Minev, I. R. et al., "Electronic dura mater for long-term multimodal neural interfaces," Science Magazine, vol. 347, No. 6218, (Jan. 9, 2015), 64 pages.
Minoux, M., Accelerated greedy algorithms for maximizing submodular set functions. Optimization Techniques, LNCS, (1978), pp. 234-243.
Moraud, E. et al., "Mechanisms Underlying the Neuromodulation of Spinal Circuits for Correcting Gait and Balance Deficits after Spinal Cord Injury," Neuron, vol. 89, No. 4, Published Online Feb. 4, 2016, (Feb. 17, 2016), 15 pages.
Murg, M. et al., "Epidural electric stimulation of posterior structures of the human lumbar spinal cord: 1. Muscle twitches—a functional method to define the site of stimulation", Spinal Cord, vol. 38, (2000), pp. 394-402.
Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.
Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.
Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.
Nandra, M. S. et al., "A parylene-based microelectrode array implant for spinal cord stimulation in rats", Conference Proceedings IEEE Eng. Med. Biol. Soc., (2011), pp. 1007-1010.
Nandra, M. S. et al., "A wireless microelectrode implant for spinal cord stimulation and recording in rats", Presentation Abstract, 2013.
Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.
Pearson, K. G., "Generating the walking gait: role of sensory feedback," Progress in Brain Research, vol. 143, Chapter 12, Published Online Nov. 28, 2003, (2004), 7 pages.
Pratt, G. et al., "Stiffness Isn't Everything," Proceedings of the Fourth International Symposium on Experimental Robotics, (Jun. 30, 1995), 6 pages.
Pratt, J. et al., "Series elastic actuators for high fidelity force control," Industrial Robot: An International Journal, vol. 29, No. 3, Available as Early as Jan. 1, 2002, (1995), 13 pages.
Prochazka, A. et al., "Ensemble firing of muscle afferents recorded during normal locomotion in cats," The Journal of Physiology, vol. 507, No. 1, (Feb. 15, 1998), 12 pages.
Prochazka, A. et al., "Models of ensemble filing of muscle spindle afferents recorded during normal locomotion in cats," The Journal of Physiology, vol. 507, No. 1, (Feb. 15, 1998), 15 pages.
Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.
Rasmussen, C. E. et al., "Gaussian Processes for Machine Learning", The MIT Press, Cambridge, Massachusetts, (2006), 266 pages.
Rasmussen, C. E. et al., "Gaussian Processes for Machine Learning (GPML) Toolbox", The Journal of Machine Learning Research, vol. 11, (2010), pp. 3011-3015.
Rasmussen, C. E. "Gaussian Processes in Machine Learning", L.N.A.I., vol. 3176, (2003) pp. 63-71.
Rattay, F. et al., "Epidural electrical stimulation of posterior structures of the human lumbosacral cord: 2. Quantitative analysis by computer modeling", Spinal Cord, vol. 38, (2000), pp. 473-489.
Reinkensmeyer, D. et al., "Tools for understanding and optimizing robotic gait training," Journal of Rehabilitation Research & Development, vol. 43, No. 5, (Aug. 2006), 14 pages.
Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.
Robbins, H., "Some Aspects of the Sequential Design of Experiments", Bull. Amer. Math. Soc., vol. 58, (1952), pp. 527-535.
Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Ryzhov, I. O. et al., "The knowledge gradient algorithm for a general class of online learning problems", Operations Research, vol. 60, No. 1, (2012), pp. 180-195.
Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.

(56) References Cited

OTHER PUBLICATIONS

Srinivas, N. et al., "Gaussian process optimization in the bandit setting: No regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.
Sun, F. et al., "Sustained axon regeneration induced by co-deletion of PTEN and SOCS3", Nature, vol. 480, No. 7377, Published Online Nov. 6, 2011, (Dec. 15, 2011), 12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Vallery, H. et al., "Compliant Actuation of Rehabilitation Robots," IEEE Robotics & Automation Magazine, vol. 15, No. 3, (Sep. 12, 2008), 10 pages.
Van Den Brand, R. et al., "Restoring Voluntary Control of Locomotion after Paralyzing Spinal Cord Injury," Science Magazine, vol. 336, No. 6085, (Jun. 1, 2012), 5 pages.
Wan, D. et al., "Life-threatening outcomes associated with autonomic dysreflexia: A clinical review," Journal of Spinal Cord Medicine, vol. 37, No. 1, (Jan. 2014), 9 pages.
Ward, A. R., "Electrical Stimulation Using Kilohertz-Frequency Alternating Current", Physical Therapy, vol. 89, Published online Dec. 18, 2008, (2009), pp. 181-190.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.
Wenger, N. et al. "Closed-loop neuromodulation of spinal sensorimotor circuits controls refined locomotion after complete spinal cord injury" Sci Transl. Med., vol. 6, Issue 255, Sep. 24, 2014), 10 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.
Anderson, K. "Targeting Recovery: Priorities of the Spinal Cord Injured Population", Journal of Neurotrauma, vol. 21, No. 10, (Oct. 2004), 13 pages.
Ateh, D. D. et al., "Polypyrrole-based Conducting Polymers and Interactions with Biological Tissues", Journal of the Royal Society Interface, vol. 3, (Jun. 22, 2006), pp. 741-752.
Axisa, F. et al., "Elastic and Conformable Electronic Circuits and Assemblies using MID in polymer", 6th International Conference on Polymers and Adhesives in Microelectronics and Photonics, IEEE Polytronic 2007 Conference, (Jan. 1, 2007), pp. 280-286.
Bizzi, E. et al., "Modular Organization of Motor Behavior", Trends in Neurosciences, vol. 18, No. 10, (Oct. 1995), 8 pages.
Burke, R., "Group Ia Synaptic Input to Fast and Slow Twitch Motor Units of Cat Triceps Surae", The Journal of Physiology, vol. 196, vol. 3, (Jun. 1, 1968), 26 pages.
Capogrosso, M. et al., "A Brain-Spinal Interface Alleviating Gait Deficits after Spinal Cord Injury in Primates", Nature, vol. 539, No. 7628, (Nov. 10, 2016), 39 pages.
Chatagny, P. et al., "Distinction between hand dominance and hand preference in primates: a behavioral investigation of manual dexterity in nonhuman primates (macaques) and human subjects", Brain and Behavior, vol. 3, No. 5, (Sep. 2013), 21 pages.
Communication Pursuant to Article 94(3) EPC in related European Patent Application No. 20160841.1 mailed Mar. 6, 2024, 5 pages.
Communication Pursuant to Article 94(3) EPC in related European Patent Application No. 21660801.7 mailed Mar. 7, 2024, 6 pages.
Communication Pursuant to Article 94(3) EPC in related European Patent Application No. 20726108.2 mailed Mar. 20, 2024, 4 pages.
Communication Regarding Extended European Search Report in related European Patent Application No. 19211738.0 mailed May 27, 2020, 8 pages.
Communication Regarding Extended European Search Report in related European Patent Application No. 18173218.1 mailed Jan. 7, 2019, 6 pages.
Communication Regarding Extended European Search Report in related European Patent Application No. 23189900.6 mailed Jan. 15, 2024, 7 pages.
Communication Regarding Extended European Search Report in related European Patent Application No. 19211738.0 mailed May 20, 2020, 8 pages.
Communication Regarding Extended European Search Report in related European Patent Application No. 24153829.7 mailed May 22, 2024, 8 pages.
Communication Regarding Extended European Search Report in related European Patent Application No. 20020190.3 mailed Oct. 5, 2020, 7 pages.
Cotton, D. P. J. et al., "A Multifunctional Capacitive Sensor for Stretchable Electronic Skins", IEEE Sensors Journal, IEEE Service Center, New York, NY, vol. 9, No. 12, (Dec. 1, 2009), pp. 2008-2009.
Cyganowski, A. et al., "Stretchable electrodes for neuroprosthetic interfaces," Sensors, 2012 IEEE, Taipei, (2012), pp. 1-4.
Dominici, N. et al., "Versatile robotic interface to evaluate, enable and train locomotion and balance after neuromotor disorders", Nature Medicine, vol. 18, No. 7, Jul. 2012, Published Online May 31, 2012, 8 pages.
Dunne, L. et al., "Initial development and testing of a novel foam-based pressure sensor for wearable sensing," Journal of NeuroEngineering and Rehabilitation, vol. 2, No. 4, (2005), 7 pages.

(56) References Cited

OTHER PUBLICATIONS

Feng, G. H. et al., "Universal concept for fabricating micron to millimeter sized 3-D parylene structures on rigid and flexible substrates," in Proc. IEEE 15th Internal Conference on Micro Electro Mechanical System, Kyoto, Japan, (2003), pp. 594-597.

Gerasimenko, Y. et al., "Spinal cord reflexes induced by epidural spinal cord stimulation in normal awake rats", Journal of Neuroscience Methods, vol. 157, No. 2, Oct. 30, 2006, 11 pages.

Graf, N. et al., "Electrochemically Stimulated Release from Liposomes Embedded in a Polyelectrolyte Multilayer", Advanced Functional Materials, vol. 21, (2011), pp. 1666-1672.

Graz, I. et al., "Flexible ferroelectret field-effect transistor for large-area sensor skins and microphones," Applied Physics Letters, American Institute of Physics, vol. 89, No. 7, (2006), pp. 73501-1-73501-3.

Graz, I. et al., "Silicone substrate within situ strain relief for stretchable thin-film transistors", Applied Physics Letters, AIP, American Institute of Physics, vol. 98, No. 12, (Mar. 22, 2011),pp. 124101-124101.

Harkema, S. et al., "Normalization of Blood Pressure with Spinal Cord Epidural Stimulation After Severe Spinal Cord Injury", Frontiers in Human Neuroscience, (Mar. 8, 2018), 11 pages.

International Search Report and Written Opinion issued in related PCT Application No. EP2017/083478, mailed May 3, 2018, 10 pages.

International Search Report and Written Opinion issued in related PCT Application No. EP2018/082942, mailed Feb. 14, 2019, 12 pages.

International Search Report and Written Opinion issued in related PCT Application No. EP2020/063563, mailed Jul. 30, 2020, 14 pages.

International Search Report and Written Opinion issued in related PCT Application No. EP2020/063564, mailed Sep. 11, 2020, 14 pages.

Jenny, A. et al., "Principles of Motor Organization of the Monkey Cervical Spinal Cord", The Journal of Neuroscience, vol. 3, No. 4, (Mar. 1983), 9 pages.

Krassioukov, A. et al., "A Systematic Review of the Management of Autonomic Dysreflexia Following Spinal Cord Injury", Archives of Physical Medicine and Rehabilitation, vol. 90, No. 4, (Apr. 2009), 27 pages.

Krassioukov, A. et al., "A Systematic Review of the Management of Orthostatic Hypotension Following Spinal Cord Injury", Archives of Physical Medicine and Rehabilitation, vol. 90, No. 5 (May 9), 22 pages.

Lacour, S. et al., "Flexible and stretchable micro-electrodes for in vitro and in vivo neural interfaces", Med. Biol. Eng. Comput., vol. 48, (2010), pp. 945-954.

Lacour, S. et al., "Stretchable gold conductors on elastomeric substrates", Applied Physics Letters, vol. 82, No. 15, (Apr. 14, 2003), pp. 2404-2406.

Levine, A. et al., "Identification of cellular node for motor control pathways", Nature Neuroscience, vol. 17, No. 4, Available Online Mar. 9, 2014, (Apr. 2024), 22 pages.

Meacham, K. W. et al., "A lithographically-patterned, elastic multi-electrode array for surface stimulation of the spinal cord," Biomed Microdevices, vol. 10, (2008), pp. 259-269.

Metzger et al., "Flexible-foam-based capacitive sensor arrays for object detection at law cost," Applied Physics Letters, American Institute of Physics, vol. 92, No. 1, (2008), pp. 13506-1-13506-3.

Minev, I. R. et al., "Evaluation of an Elastomer Based Gold Microelectrode Array for Neural Recording Applications," Proceedings of the 5th International IEEE/EMBS Conference on Neural Engineering, Cancun, Mexico, (Apr. 27-May 1, 2011), pp. 482-485.

Minev, I. R. et al., "High sensitivity recording of afferent nerve activity using ultra-compliant microchannel electrodes: an acute in vivo validation," J. Neural Eng., (2012), vol. 9, No. 1-7.

Oxford English Dictionary Definition of "Inserted" (Year: 2020), 2 pages.

Park, K. J. et al., "Continuous "Over and Over" Suture for Tricuspid Ring Annuloplasty", Korean Journal of Thoracic and Cardiovascular Surgery, vol. 45, (2012), pp. 19-23.

Pellinen, D. S. et al., "Multifunctional Flexible Parylene-Based Intracortical Microelectrodes", Proceedings of the 2005 IEEE: Engineering in Medicine and Biology 27th Annual Conference, Sep. 1-4, (2005), pp. 5272-5275.

Pflug, H. et al., "Parallel Resonant Inductive Wireless Power Transfer", IEEE, Proceedings of Wireless Power Week 2019, London, United Kingdom (Jun. 17, 2019), pp. 182-187.

Phillips, A et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.

Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.

Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.

Robinson, A. et al., "Hybrid stretchable circuits on silicone substrate," Journal of Applied Physics, vol. 11, No. 5, (2014), 5 pages.

Schmidlin, E. et al., "Behavioral Assessment of Manual Dexterity in Non-Human Primates", Journal of Visualized Experiments, vol. 57, No. e3258, Nov. 11, 2011, 11 pages.

Sherman, J. et al., "Measurements of the normal cervical spinal cord on MR Imaging", American Journal of Neuroradiology, vol. 11, No. 2, Mar. 1990, 4 pages.

Suzuki, T. et al., "A 3D flexible parylene probe array for multi-channel neural recording", IEEE Neural Eng., (2003), pp. 154-156.

Takeuchi, S. et al., "3D flexible multichannel neural probe array", J. Micromech. Microeng., vol. 14, No. 104-107, (2004), 4 pages.

Wei, P. et al., "Stretchable microelectrode array using room-temperature liquid alloy interconnects", Journal of Micromechanics and Microengineering, vol. 21, No. 054015, (2011), pp. 1-8.

Hohenschurz-Schmidt, D. J. et al., Linking Pain Sensation to the Autonomic Nervous System: The Role of the Anterior Cingulate and Periaqueductal Gray Resting—State Networks, Front Neuroscience, Feb. 27, 2020, vol. 14, No. 147, 15 pages.

Andersson, K.-E. et al., "CNS Involvement in Overactive Bladder—Pathophysiology and Opportunities for Pharmacological Intervention", Drugs, vol. 63, No. 23, (2003), pp. 2595-2611.

Augustine, G. J. et al., "Autonomic Regulation of the Bladder", Neuroscience, $2^{nd}$ edition, Chapter Twenty-One, Sunderland, (MA), Dec. 4, 2022, 5 pages.

Coursera, (n.d.), What is Machine Learning? Definition, Types, and Examples. Coursera. https://www.coursera.org/articles/what-is-machine learning, (Year: 2023), 12 pages.

Courtine, G. et al., "Modulation of multisegmental monosynaptic responses in a variety of leg muscles during walking and running in humans", Journal of Physiology, (2007), vol. 582, No. 3, pp. 1125-1139.

Danner, S. M. et al., "Can the Human Lumbar Posterior Columns be Stimulated by Transcutaneous Spinal Cord Stimulation? A modeling study", Europe PMC funders author manuscripts, Artificial Organs, (2011), vol. 35, No. 3, pp. 257-262.

Desantana, J. M. et al., "Effectiveness of Transcutaneous Electrical Nerve Stimulation for Treatment of Hyperalgesia and Pain", Curr Rheumatol Rep., (2008), vol. 10, pp. 492-499.

Drummond, G. B. et al., "Thoracic impedance used for measuring chest wall movement in postoperative patients", British Journal of Anaesthesia, (1996), vol. 77, pp. 327-332.

Dubinsky, R. M. et al., "Assessment: Efficacy of transcutaneous electric nerve stimulation in the treatment of pain in neurologic disorders (an evidenced-based review)", Report of the Therapeutics and Technology Assessment Subcommittee of the American Academy of Neurology, Neurology, (2010), vol. 74, pp. 173-176.

Edgerton, V. R. et al., "Epidural stimulation of the spinal cord in spinal cord injury: current status and future challenges", Expert Rev.

(56) References Cited

OTHER PUBLICATIONS

Neurother, doi: 10.1586/ern. 11.129 [NIH Public Access—Author Manuscript—5 pages], (Oct. 2011), vol. 11, No. 10, pp. 1351-1353.
Extended European Search Report issued in counterpart European Patent Application No. 23189900.6 dated Jan. 4, 2024, 7 pages.
European Examination Report in counterpart European Patent Application No. 17826212.7 mailed Dec. 21, 2020, 7 pages.
European Office Action and Annex issued in counterpart European Patent Application No. 18807366.2 mailed Mar. 22, 2023, European Patent Office, Munich, Germany, 4 pages.
EPO Communication and Supplementary European Search Report issued in counterpart European Patent Application No. 17745012.9 mailed Aug. 3, 2019, pp. 1-8.
European Opposition filed in counterpart European Patent Application No. 17826212.7 on Dec. 2, 2022, 56 pages.
Fong, A. J. et al., "Recovery of control of posture and locomotion after a spinal cord injury: solutions staring US in the face", Progress in Brain Research, Elsevier Amsterdam, Netherlands, (2009), vol. 175, Chapter 25, pp. 393-418.
Gerasimenko, Y. et al., "Novel and Direct Access to the Human Locomotor Spinal Circuitry", Journal of Neuroscience, (Mar. 10, 2010), vol. 30, No. 10, pp. 3700-3708.
Gerasimenko, Y. P. et al., "Epidural Spinal Cord Stimulation Plus Quipazine Administration Enable Stepping Complete Spinal Adult Rats", J. Neurophysiol., (2007), vol. 98, pp. 2525-2536.
Gerasimenko, Y. et al., "Initiation and modulation of locomotor circuitry output with multisite transcutaneous electrical stimulation of the spinal cord in noninjured humans", J. Neurophysiol., (2015), vol. 113, pp. 834-842.
Gerasimenko, Y. et al., "Transcutaneous electrical spinal-cord stimulation in humans", Ann Phys Rehabil. Med., (2015), vol. 58, No. 4, pp. 225-231.
Giuliano, F. et al. "Neural Control of Erection", Physiology & Behavior, vol. 83, No. 2, (Nov. 15, 2004), pp. 189-201.
Hovey, C. et al., "The New Guide to Magnet Stimulation", The Magstim Company Ltd., (Jul. 21, 2006), 45 pages.
International Search Report and Written Opinion issued in related PCT Application No. PCT/US2017/015435, mailed May 8, 2017, 9 pages.
International Search Report and Written Opinion issued in related PCT Application No. PCT/EP2020/053381, mailed May 12, 2020, 8 pages.
International Search Report and Written Opinion issued in related PCT Application No. PCT/EP2018/082939, mailed Feb. 14, 2019, 11 pages.
Iyer, P. C. et al., "Characterization of stimulus response curves obtained with transcranial magnetic stimulation from bilateral tibialis anterior muscles post stroke", Neuroscience Letters, vol. 713, (2019), pp. 134530.
Jaman, R., (2022), A retrospective cross-sectional survey of lumbosacral recorded at the D.U.T. Chiropractic Day Clinic (1995-2005), https://doi.org/10.51415/10321/221, (Year: 2014), 94 pages.
Krenn, M. et al., "Selectivity of transcutaneous stimulation of lumbar posterior roots at different spinal levels in humans.", Biomed Tech (2013), 58 (Suppl. 1), DOI 10.1515/bmt- 2013-4010, 2 pages.
Ichiyama, R. M. et al., "Hindlimb stepping movements in complete spinal rats induced by epidural spinal cord stimulation", Neuroscience Letters, (2005), vol. 383, pp. 339-344.
Kapetanakis, S. et al., "Cauda Equina Syndrome Due to Lumbar Disc Herniation: a Review of Literature", Folia Medica, (Dec. 22, 2017), vol. 59, No. 4, pp. 377-386.
Kirazli, O. et al., "Anatomy of the spinal dorsal root entry zone: its clinical significance", Acta Neurochir, vol. 156, (2014), pp. 2351-2358.
Kitano, K. et al., "Spinal reflex in human lower leg muscles evolved by transcutaneous spinal cord stimulation", Journal of Neuroscience Methods, (2009), vol. 180, pp. 111-115.
Kondo, et al., "Laser monitoring of chest wall displacement", Eur. Respir. J., (1997), vol. 10, pp. 1865-1869.

Korean Intellectual Property Office (KIPO) International Search Report and Written Opinion issued in counterpart PCT Application No. PCT/US2017/015435 mailed May 8, 2017, pp. 1-11.
Lu, D. et al., "Engaging cervical spinal cord networks to re-enable volitional control of hand function in tetraplegic patients", Neurorehabilitation and Neural Repair, vol. 30, No. 10, Available Online May 18, 2016, Nov. 2016, 21 pages.
Minassian, K. et al., "Transcutaneous spinal cord stimulation", International Society for Restoration Neurology, (Aug. 2011), 6 pages.
Minassian, K. et al. "Posterior root-muscle reflexes elicited by transcutaneous stimulation of the human lumbosacral cord", Muscle and Nerve, (Mar. 2007), vol. 35, pp. 327-336.
Nandra, M. et al., "Microelectrode Implants for Spinal Cord Stimulation in Rats", Doctor of Philosophy Thesis, California Institute of Technology, (2014), 104 pages.
Needle, A. R. et al., "Brain Regulation of muscle tone in healthy and functionally unstable ankles", Journal of Sport Rehabilitation, (2013), vol. 22, No. 1, pp. 202-211.
Niu, T. et al., "A Proof-of-Concept Study of Transcutaneous Magnetic Spinal Cord Stimulation for Neurogenic Bladder", Scientific Reports, (2018), vol. 8, 12549, (12 pages).
[No Author], National Health Service, "Lumbar Decompression Surgery: When it's used", NHS, Apr. 28, 2022, https://www.nhs.uk/conditions/lumbar-decompression-surgery/why-its-done/#:—:text=Cauda%equina%20syndrome%20is%20severe%20or%20getting20% worse, 2 pages.
[No Author], Vital Signs—Cleveland Clinic [Retrieved on Nov. 22, 2021], Retrieved from the Internet: URL:https://my.clevelandclinic.org/health/articles/10881-vital-signs, 7 pages.
Roy, F. D. et al., "Effect of percutaneous stimulation at different spinal levels on the activation of sensory and motor roots", Exp. Brain Res., (2012), vol. 223, pp. 281-289.
Sayenko, D. G. et al., "Neuromodulation of evoked muscle potentials induced by epidural spinal-cord stimulation in paralyzed individuals", J. Neurophysiol., (2014), vol. 111, pp. 1088-1099.
Sayenko, D. G. et al., "Spinal segment-specific transcutaneous stimulation differentially shapes activation pattern among motor pools in humans", (2015), J. Appl. Physiol., vol. 118, pp. 1364-1374.
Seifert, H. M. et al., "Restoration of Movement Using Functional Electrical Stimulation and Bayes' Theorem", The Journal of Neuroscience, (Nov. 1, 2022), vol. 22, No. 21, pp. 9465-9474.
Shafik, A. et al., "Magnetic stimulation of the cavernous nerve for the treatment of erectile dysfunction in humans", International Journal of Impotence Research, (2000), vol. 12, pp. 137-142.
Shafik, A. et al., "Extrapelvic cavernous nerve stimulation in erectile dysfunction. Human Study", Andrologia, (1996), vol. 28, No. 3, pp. 151-156. Doi: 10.1111/j. 1439-0272. 1996.tb02774.x [Abstract—2 pages].
Sharpe, A. et al., "Upper-limb muscles responses to epidural, subdural and intraspinal stimulation of the cervical spinal cord", Journal of Neural Engineering, vol. 11, No. 1, Feb. 2014, 16 pages.
Szava, Z. et al., "Transcutaneous electrical spinal cord stimulation: Biophysics of a new rehabilitation method after spinal cord injury", (Jan. 2011), ISBN: 978-3-639-34154-6, 95 pages.
Tanabe, S. et al., "Effects of transcutaneous electrical stimulation combined with locomotion-like movement in the treatment of post-stroke gait disorder: a single-case study", (2008), vol. 30, No. 5, 411-416 Abstract, 1 page.
Temel, Y. et al., "Case Report—Deep brain stimulation of the thalamus can influence penile erection", International Journal of Impotence Research, vol. 16, pp. 91-94.
Troni, W. et al., "A methodological reappraisal of non invasive high voltage electrical stimulation of lumbosacral nerve roots", Clin. Neurophysiol., (2011), vol. 122, pp. 2071-2080.
Wang, T. et al., "Incidence of C5 nerve root palsy after cervical surgery—A meta-analysis for decade", Medicine, (2017), vol. 96, No. 45, 14 pages.
Ward, A. R., "Electrical Stimulation Using Kilohertz-Frequency Alternating Current", Phys Ther., (Feb. 2009), vol. 89, No. 2, pp. 181-190, [published online Dec. 18, 2008].

(56) References Cited

OTHER PUBLICATIONS

Communication Regarding Extended European Search Report in related European Patent Application No. 19209911.7 mailed Mar. 1, 2023, 2 pages.
"Health Journalism Glossary: Bidirectional", Association of Health Care Journalist (AHCJ), 2024, 3 pages.
Anonymous, "Re: Round corners (fillet) in Illustrator CS6", in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.
Anonymous, Vital Signs, Datasheet [online], Cleveland Clinic [retrieved on Nov. 22, 2021]. Retrieved from the Internet: <URL:https://my.clevelandclinic.org/health/articles/10881-vital-signs, 19 pages.
Bruckenstein, S. et al., "An experimental study of nonuniform current distribution at rotating disk electrodes", Journal of the Electrochemical Society, (1970), vol. 117, No. 8, pp. 1044-1048.
Communication Pursuant to Article 94(3) EPC in counterpart European Application No. 19209911.7 mailed Jul. 20, 2023, 5 pages.
Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12847885.6 mailed Apr. 15, 2016, 5 pages.
Communication Pursuant to Article 94(3) EPC in counterpart European Patent Application No. 12847885.6 mailed Feb. 16, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 14765477.6 mailed Nov. 14, 2018, 5 pages.
Communication Pursuant to Article 94(3) EPC in counterpart European Patent Application No. 14765477.6 mailed Sep. 27, 2019, 6 pages.
Communication Pursuant to Article 94(3) EPC in counterpart European Patent Application No. 14849355.4 mailed Jul. 20, 2018, 6 pages.
Communication Pursuant to Article 94(3) EPC in counterpart European Patent Application No. 15834593.4 mailed Jul. 17, 2019, 4 pages.
Communication Pursuant to Article 94(3) EPC in counterpart European Patent Application No. 15834593.4 mailed Jul. 30, 2020, 5 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
Communication Pursuant to Rule 114(2) EPC in counterpart European Patent Application No. 12847885.6 mailed Mar. 27, 2015, 28 pages.
Decision to Refuse a European Patent Application in counterpart European Patent Application No. 15834593.4 mailed Oct. 28, 2021, 24 pages.
European Reply to Communication in counterpart European Patent Application No. 12847885.6 mailed Oct. 24, 2016, 4 pages.
Extended European Search Report in counterpart European Patent Application No. 14765477.6 mailed Nov. 8, 2016, 10 pages.
Extended European Search Report in counterpart European Patent Application No. 14849355.4 mailed May 10, 2017, 7 pages.
Extended European Search Report in counterpart European Patent Application No. 15834593.4 mailed Apr. 4, 2018, 7 pages.
Extended European Search Report in counterpart European Patent Application No. 15836927.2 mailed Mar. 1, 2018, 9 pages.
Extended European Search Report in counterpart European Patent Application No. 16825005.8 mailed Feb. 19, 2019, 8 pages.
Extended European Search Report in counterpart European Patent Application No. 16833973.7 mailed Dec. 13, 2018, 6 pages.
Extended European Search Report in counterpart European Patent Application No. 18744685.1 mailed Sep. 7, 2020, 8 pages.
Extended European Search Report in counterpart European Patent Application No. 19201998.2 mailed Apr. 21, 2020, 7 pages.
Extended European Search Report in counterpart European Patent Application No. 19851613.0 mailed Apr. 19, 2022, 9 pages.
Extended European Search Report in counterpart European Patent Application No. 19852797.0 mailed Apr. 19, 2022, 6 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.
Extended European Search Report in counterpart European Patent Application No. 20175385.2 mailed Jan. 22, 2021, 8 pages.
Extended European Search Report in counterpart European Patent Application No. 21166801.7 mailed Aug. 17, 2021, 11 pages.
Extended European Search Report in counterpart European Patent Application No. EP12847885.6 mailed May 6, 2015, 7 pages.
Extended European Search Report in counterpart European Patent Application No. 19211698.6 mailed May 28, 2020, 6 pages.
Ginsbourger, D. et al., "Kriging is well-suited to parallelize optimization", Computational Intelligence in Expensive Optimization Problems, Berlin, Heidelberg: Springer Berlin Heidelberg, (2010), Ch. 6, pp. 131-162.
Hung, C. C. et al., "Transparent microprobe array fabricated by MEMS hot embossing technology for photodynamic therapy application", IEICE Electronics Express, (2010), vol. 7, No. 9, pp. 569-576.
International Search Report and Written Opinion issued in counterpart PCT Application No. PCT/US2012/064878 mailed Mar. 19, 2013, 11 pages.
International Search Report and Written Opinion issued in counterpart PCT Application No. PCT/US2014/029340 mailed Aug. 6, 2014, 11 pages.
International Search Report and Written Opinion issued in counterpart PCT Application No. PCT/US2014/057886 mailed Dec. 24, 2014, 6 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2015/046378 mailed Dec. 1, 2015, 5 pages.
International Search Report and Written Opinion issued in counterpart PCT Application No. PCT/US2015/047268 mailed Dec. 8, 2015, 17 pages.
International Search Report and Written Opinion issued in counterpart PCT Application No. PCT/US2015/047272 mailed Dec. 3, 2015, 11 pages.
International Search Report and Written Opinion issued in counterpart PCT Application No. PCT/US2016/041802 mailed Sep. 12, 2016, 17 pages.
International Search Report and Written Opinion issued in counterpart PCT Application No. PCT/US2016/045898 mailed Dec. 5, 2016, 13 pages.
International Search Report and Written Opinion issued in counterpart PCT Application No. PCT/US2016/049129 mailed Dec. 5, 2016, 13 pages.
International Search Report and Written Opinion issued in counterpart PCT Application No. PCT/US2018/015098 mailed Mar. 12, 2018, 9 pages.
International Search Report and Written Opinion issued in counterpart PCT Application No. PCT/US2018/033942 mailed Aug. 31, 2018, 8 pages.
International Search Report and Written Opinion issued in counterpart PCT Application No. PCT/US2019/047551 mailed Nov. 21, 2019, 9 pages.
International Search Report and Written Opinion issued in counterpart PCT Application No. PCT/US2019/047777 mailed Nov. 14, 2019, 15 pages.

(56) References Cited

OTHER PUBLICATIONS

International Search Report and Written Opinion issued in counterpart PCT Application No. PCT/US2020/033830 mailed Oct. 14, 2020, 10 pages.
International Search Report and Written Opinion issued in counterpart PCT Application No. PCT/US2022/024673 mailed Jun. 28, 2022, 8 pages.
International Search Report issued in counterpart PCT Application No. PCT/US2012/020112 mailed Jul. 30, 2012, 4 pages.
International Search Report issued in counterpart PCT Application No. PCT/US2012/022257 mailed Sep. 3, 2012, 4 pages.
International Search Report issued in counterpart PCT Application No. PCT/US2012/030624 mailed Oct. 31, 2012, 3 pages.
International Search Report issued in counterpart PCT Application No. PCT/US2012/064874 mailed Mar. 19, 2013, 4 pages.
Jonic, S. et al., "Three machine learning techniques for automatic determination of rules to control locomotion", IEEE Transactions on Biomedical Engineering, (1999), vol. 46, No. 3, pp. 300-310.
Kim, W. S. et al., "Ultra-sensitive Flexible Pressure Sensor with Stamped Polyurethane Rubber", 2011 11th IEEE Conference on Nanotechnology, (2011), pp. 1607-1610.
Kim, Y. et al., "Electrical behavior of defibrillation and pacing electrodes", Proceedings of the IEEE, (2002), vol. 84, No. 3, pp. 446-456.
Minassian, K. et al., "Human Lumbar Cord Model of the Locomotor Central Pattern Generator", Second Congress International Society of Intraoperative Neurophysiology (ISIN), (2009), pp. 11-13.
Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.
Peachpit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.
Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.
Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.
Valchinov, E. S. et al., "An active electrode for biopotential recording from small localized bio-sources", BioMedical Engineering OnLine, (2004), vol. 3, No. 25, pp. 1-14.
Wang, J. M. et al., "Gaussian process dynamical models for human motion", IEEE Transactions on Pattern Analysis and Machine Intelligence, (2007), vol. 30, No. 2, pp. 283-298.
Ward, A. R. et al., "Sensory, motor, and pain thresholds for stimulation with medium frequency alternating current", Archives of Physical Medicine and Rehabilitation, (1998), vol. 79, No. 3, pp. 273-278.
Wiley, J. D. et al., "Analysis and Control of the Current Distribution under Circular Dispersive Electrodes", Biomedical Engineering, IEEE Transactions on BME, (1982), vol. 29, No. 5, pp. 381-385.
YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.

\* cited by examiner

FIG. 8

Amplitude ⊗ 7.2 mA
Frequency ⊙ 80 Hz (±10%)

Figure 9:
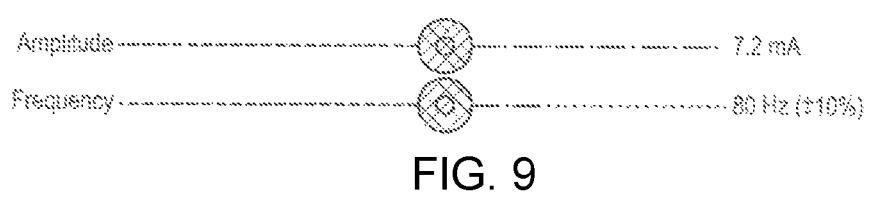

FIG. 9

NEUROMODULATION SYSTEM

CROSS-REFERENCE TO RELATED APPLICATIONS

The present application is a continuation of U.S. patent application Ser. No. 17/105,345 filed on Nov. 25, 2020, which claims priority to EP 19211738.0 entitled "Neuromodulation system" and filed Nov. 27, 2019, all of which are incorporated herein by reference in their entirety.

TECHNICAL FIELD

The present invention relates to neuromodulation systems, and more particularly, to a system for planning and/or controlling a neuromodulation system.

BACKGROUND

Neuromodulation, in particular neurostimulation, in particular electrical neurostimulation, may be applied to a subject by a neuromodulation system comprising at least one electrode array comprising at least one electrode. Neuromodulation systems may further comprise at least one of a controller, e.g. a microcontroller, a processor, e.g. a microprocessor, a pulse generator, in particular an implantable pulse generator, a sensor, a communication module, and a telemetry module.

The electrode array, e.g. comprised in a lead paddle, can be applied for percutaneous electrical stimulation, transcutaneous electrical nerve stimulation (TENS), epidural electrical stimulation (EES), subdural electrical stimulation (SES), functional electrical stimulation (FES) and/or all neurostimulation and/or muscle stimulation applications that use at least one electrode array and/or at least one electrode. Lead paddles are for example described by U.S. Pat. No. 8,108,051B2, US 2013/0096662 A1, US 2012/0006793 A1 and EP3013411A1.

Neurostimulation, in particular multi-channel and/or variable neurostimulation, often requires an interface to create the stimulation program and a stimulation system to deliver the stimulation. WO2017117450A1 generally describes a system for programming a neurostimulator including a storage device and a pattern generator. The storage device may store a pattern library and one or more neuronal network models. The pattern library may include fields and waveforms of neuromodulation. The one or more neuronal network models may each be configured to allow for evaluating effects of one or more fields in combination with one or more waveforms in treating one or more indications for neuromodulation. The pattern generator may be configured to construct and approximately optimize a spatio-temporal pattern of neurostimulation and/or its building blocks for a specified range of varying conditions using at least one neuronal network model.

EP 3 285 855 B1 generally describes a system for delivering neurostimulation including a programming control circuit and a user interface. The programming control circuit may be configured to generate stimulation parameters controlling delivery of neurostimulation pulses according to one or more stimulation waveforms associated with areas of stimulation each defined by a set of electrodes. The neurostimulation pulses are each delivered to an area of stimulation. The user interface may include a display screen and an interface control circuit. The interface control circuit may be configured to define the one or more stimulation waveforms and the areas of stimulation and may include a stimulation frequency module configured to display a stimulation rate table on the display screen. The stimulation rate table may present stimulation frequencies associated with each of the areas of stimulation for selection by a user.

EP630987 B1 generally describes an external control device for use with a neurostimulation system having a neurostimulation lead and a plurality of electrodes circumferentially disposed around the neurostimulation lead capable of conveying an electrical stimulation field into tissue in which the electrodes are implanted, comprising: a user interface including a display screen configured for displaying three-dimensional graphical renderings of the electrodes a plurality of iconic control elements graphically linked to the graphical renderings of the electrodes and indicating an amount of current through the corresponding electrode in terms of a fractionalized current value for a displayed set of stimulation parameters, and a first circumferential modification control element and a second circumferential modification control element configured for being actuated; a processor configured for generating stimulation parameters designed to modify the electrical stimulation field when the first circumferential modification control element is actuated to circumferentially contract the electrical stimulation field about a locus of the electrical stimulation field and when the second circumferential modification control element is actuated to circumferentially expand the electrical stimulation field about the locus of the electrical stimulation field; and output circuitry configured for transmitting the stimulation parameters to the neurostimulation system.

However, the user's input, i.e. the stimulation program, may not necessarily match the nature and capacity of the electrode array, resulting in a conflict in terms of feasibility of the stimulation program.

SUMMARY

Provided is a neuromodulation system which allows finely tuned neuromodulation with regard to the feasibility of the planned stimulation program. The neuromodulation system may include one or more components or modules including, but not limited to, an input module for inputting a planned neuromodulation event or a series of neuromodulation events, an analyzing module for analyzing a neuromodulation event or a series of neuromodulation events, in which the analyzing module and the input module are connected such that the input module is configured to forward the planned neuromodulation event or a series of neuromodulation events to the analyzing module and the analyzing module is configured to analyze the planned neuromodulation event or a series of neuromodulation events regarding one or more possible neuromodulation conflict(s).

While the neuromodulation system may be used for any purpose, in some aspects, the neuromodulation system may be used for restoring autonomic function and/or motoric function. In some embodiments, the neuromodulation system may also be used in a decoupled manner to set a neuromodulation system based on patient data and/or feedback information, e.g. as a generic system decoupled from an implanted neuromodulation system. In some embodiments, the neuromodulation system may be a neurostimulation system.

In some aspects, the neuromodulation system may be used for percutaneous electrical stimulation, TENS, EES, SES, FES and/or all neurostimulation and/or muscle stimulation applications that use at least one electrode array and/or at least one electrode. The neuromodulation system may be a closed-loop system or an open-loop system.

The neuromodulation system may be used in a method for the treatment of motor impairment and/or restoring motor function. Motor function may comprise all voluntary postures and movement patterns, such as locomotion. In additional aspects, the neuromodulation system may be used in a method for the treatment of autonomic dysfunction and/or restoring autonomic function. Autonomic dysfunction may comprise altered and/or impaired regulation of at least one of blood pressure, heart rate, thermoregulation (body temperature), respiratory rate, immune system, gastro-intestinal tract (e.g. bowel function), metabolism, electrolyte balance, production of body fluids (e.g. saliva and/or sweat), pupillary response, bladder function, sphincter function and sexual function. In further aspects, the neuromodulation system may be used in a method for the treatment of autonomic dysreflexia, spasticity, altered and/or impaired sleep behavior and/or pain.

A neuromodulation event may be or may comprise start, stop, up ramping, down ramping, duration, repetition and/or cycles of stimulation of at least one muscle and/or stimulation block. A series of neuromodulation events can also be referred to as stimulation program and/or stimulation partiture.

By analyzing any potential conflict(s) between a planned neuromodulation event or a series of neuromodulation events and boundary conditions of the planned neuromodulation, e.g. system-related, patient-related, or user made, before the beginning of the neurostimulation, the neurostimulation outcome (e.g. of a patient) closest to the planned neuromodulation event or a series of neuromodulation events and feasible with the boundary conditions and/or any type of preestablished limitation, may be enabled. In some embodiments, the conflicts may be analyzed before the stimulation settings are uploaded to a controller and/or a pulse generator.

A stimulation block determines an electrode configuration and/or stimulation configuration, and/or an amplitude/intensity of stimulation and a pulse train, wherein a pulse train may be defined as a temporal arrangement of stimulation events. During movement, e.g. a gait cycle, different stimulation blocks need to be stimulated consequentially and/or at least partially simultaneously with different pulsed electrical waveforms at different frequencies and amplitudes, sometimes with different pattern of pulses, in order to reproduce a movement, e.g. a gait cycle comparable to a healthy subject. The neurostimulation system may be or may comprise a pulse generator, in some embodiments an implantable pulse generator (IPG) and/or non-implantable pulse generator. The neurostimulation system may comprise a lead and/or an electrode array comprising at least one electrode, preferably multiple electrodes. The neurostimulation system may further comprise a controller, a microcontroller, a processor, a microprocessor, a communication system, a telemetry system, a sensor, a sensor network, a display, and/or a training device. Collectively, the various tangible components or a subset of the tangible components may be referred to herein as "logic" configured or adapted in a particular way, for example as logic configured or adapted with particular software or firmware. In some aspects, logic and memory may be integrated into one or more common devices, such as an application specific integrated circuit, field programmable gate array, or a system on a chip.

The input module may be or may comprise a user interface, in some embodiments a graphical user interface. In some embodiments, the input module may enable verification and optimization of a neuromodulation program (also referred to as stimulation partiture) and/or neuromodulation settings. In some embodiments, a user, e.g. a therapist, physiotherapist, medical doctor, nurse, patient and/or patient relative may input a stimulation program comprising a neuromodulation event or a series of neuromodulation events on the input module.

The input module sends information to an analyzing module. The analyzing module processes the stimulation program to identify conflicts in the planned neuromodulation event or series of neuromodulation events. Such conflicts may be from any source including, but not limited to, neuromodulation safety, hardware capabilities, and/or software capabilities.

The system may further comprise at least one correction module which is configured to amend the planned neuromodulation event or a series of neuromodulation events such that in case of detection of a neurostimulation conflict the neuromodulation event or a series of neuromodulation events is/are amended such that the neuromodulation conflict is avoided. In some embodiments, this may allow correction of the conflict(s) before the beginning of the planned stimulation program, the planned neuromodulation may be made compatible with the system capabilities and the patient. In some embodiments, a neurostimulation outcome may be secured by detecting conflict(s) between a planned stimulation program and a stimulation system to deliver the stimulation and by proposing an appropriate fix to resolve the conflict(s) before the planned neurostimulation program is uploaded on the stimulation system, and thus before the beginning of the planned exercise and/or physiological process. In other words, each time a new neuromodulation event and/or series of neuromodulation event is inputted, this input may be analyzed by the neuromodulation system and corrected before the stimulation is started. This ensures that after transferring the stimulation program to the stimulation system all parameters are verified. Consequently, the stimulation program can be executed by the system and is compatible with the patient.

The analysis by the analyzing module and/or the correction by the correction module may be applied to either a time segment of stimulation, e.g. a neuromodulation event, or to the complete stimulation program, e.g. a series of neuromodulation events, e.g. by looking at a variable over the complete stimulation duration instead of during a single time segment.

The neuromodulation system may further comprise output means, wherein the output means are connected to the analyzing module and which are configured to provide at least partially a visual output of at least one of the analysis performed by the analyzing module, the planned neuromodulation event or a series of neuromodulation events, the neuromodulation conflict(s), the correction of the planned neuromodulation event or a series of neuromodulation events. This may enable that a user, e.g. a physiotherapist, a therapist, a medical doctor, a patient, and/or a patient relative, may watch and/or control the analysis performed by the analyzing module, the planned neuromodulation event or a series of neuromodulation events, the neuromodulation conflict(s), the correction of the planned neuromodulation event or a series of neuromodulation events. In other words, the output means may make the neuromodulation system transparent for the user. In some embodiments, the output means may be a display and/or a touch screen and/or a graphical user interface. For example, the display may be used to present a visual representation of data using, for example, a "graphics processing unit" (GPU), a processing unit that comprises a programmable logic chip (processor) specialized for display functions. The GPU may render images, animations, and video for a computer screen. The GPU may be located on plug-in cards, in a chipset of a motherboard of a computer, or in the same chip as the central processing unit (CPU) of the device. In some aspects, the output means may alternatively be referred to as output module.

The input module, the analyzing module, the correction module and/or the output means may be implemented on a programmer, e.g. a space-time programmer (STP).

The neuromodulation system may be further configured for a semi-automatic or automatic correction of the neuromodulation conflict. In some embodiments, the amendment of the planned neuromodulation event or series of neuromodulation events may be at least partly based on an algorithm provided by the correction module. In some embodiments, semi-automatic correction may be a combination of an algorithm provided by the correction module and an intervention of a user, e.g. through the input module, in some embodiments through a user-interface such as, but not limited to, one or more user input devices, such as a keyboard, mouse, track ball, stylus, touch screen, microphone, natural user interface, etc. connected via wired or wireless connections. Semi-automatic or automatic correction of the neuromodulation conflict may enable correction within a minimum of time, such that the planned neuromodulation may be provided with no or minimum time delay, e.g. in real-time or close to real-time.

Embodiments of the present disclosure provide that there may be also a manual and/or completely manual correction functionality. Such manual correction capability can be provided alternatively or additionally. The manual correction capability can be provided through mechanisms like a tool (or several tools) and/or instructions (like instructions in a user manual) and may be provided via a user interface (e.g. a graphical user interface).

The one or more possible neuromodulation conflict(s) may be related to at least one of neuromodulation safety, hardware capabilities, and/or software capabilities. By analyzing and/or correcting conflict(s) related to neuromodulation safety, hardware capabilities and/or software capabilities, the neuromodulation system enables correction of conflicts of multiple origins, in some embodiments any form of at least partially calculable conflict source is thereby correctable.

The hardware capabilities may include capabilities of the neuromodulation system or its components, e.g. the input module, the analyzing module, the correction module, the output means, at least one of a controller, a microcontroller, a processor, a microprocessor, a communication system, a telemetry system, a sensor, a sensor network, a display, a pulse generator, a lead and/or a training device.

Correcting neuromodulation conflict(s) related to hardware capabilities may enable adequate timing between pulses provided to set the current source/voltage source to the correct value and/or delivering the required current/voltage at any given instant. Correcting neuromodulation conflict(s) related to neuromodulation safety may enable an adequate grounding time, and/or keeping electrical simulation within limited boundaries and/or comfortability. Correcting neuromodulation conflict(s) related to software capabilities may enable that the quantity of information is compatible with the memory capacity available and that, e.g. a microcontroller computational load is compatible with its speed.

The neurostimulation system may comprise a neurostimulation array, wherein the neurostimulation array may be or may comprise an array of multiple electrodes and wherein a neuromodulation conflict may be detected, when the planned neuromodulation event or a series of neuromodulation events may require an impossible electrode configuration.

In some embodiments, more than one stimulation block may be requested to be stimulated at the same time, yet the more than one stimulation block may share electrodes of the array of multiple electrodes. In some embodiments, detecting a neuromodulation conflict may enable merging the electrode configurations of the more than one stimulation block, providing an alternative electrode configuration and/or keeping the electrode configuration as planned but avoiding pulse overlap. In some embodiments this may enable creating a solution, where during the period of conflict a correction of the conflict may be enabled, enabling best possible neuromodulation.

The correction can be applied with or without display of the conflicts on the user interface, and with or without the intervention of the user through the user interface.

In some embodiments, the method may be a method for performing neuromodulation, the method comprising at least the following steps:

analyzing a neuromodulation event or a series of neuromodulation events, wherein the analyzing includes the analysis whether the planned neuromodulation event or a series of neuromodulation events comprises one or more possible neuromodulation conflict(s).

The method may further comprise the step of correcting the neuromodulation event or a series of neuromodulation events such that the one or more possible neuromodulation conflict(s) is/are avoided.

The method may be characterized in that one or more possible neuromodulation conflict(s) may be related to at least one of neuromodulation safety, hardware capabilities, software capabilities.

It is to be understood that both the foregoing general description and the following detailed description are exemplary and explanatory only and are not restrictive of the disclosed embodiments or the scope of the inventions as claimed. The concepts in this application may be employed in other embodiments without departing from the scope of the inventions.

BRIEF DESCRIPTION OF THE FIGURES

Further details and advantages of the disclosed embodiments shall now be disclosed in connection with the drawings. The accompanying drawings, which are incorporated in and constitute a part of this specification, illustrate several embodiments consistent with the disclosure and together with the description, serve to explain the principles of the disclosure. In the drawings:

Figure 8:
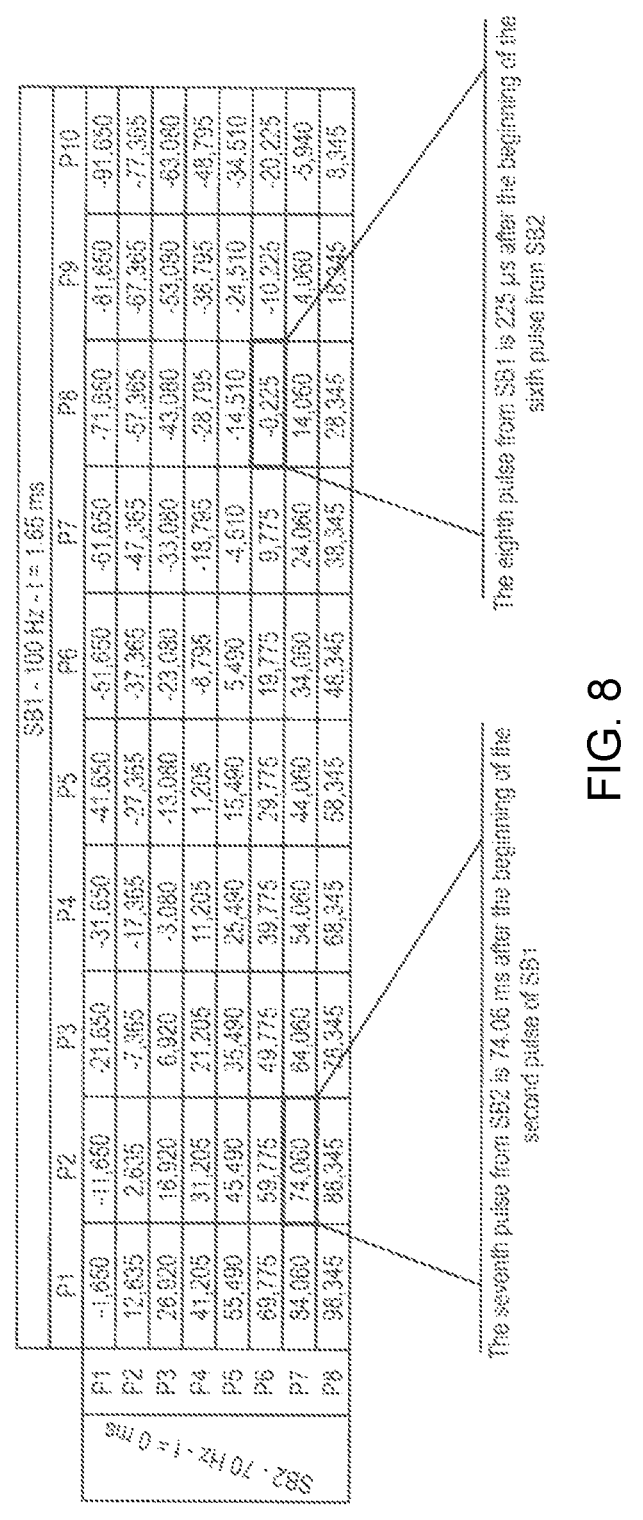

FIG. 8 depicts an exemplary embodiment of a pulse temporal distance matrix (in ms) during 100 ms for stimulation block 1 at 100 Hz starting at t=1.65 ms and stimulation block 2 at 70 Hz starting at t=0 ms, according to the present invention;

FIG. 9 depicts an example of how the output means of the system could communicate an internal acceptable variation of the frequency, according to the present invention;

DETAILED DESCRIPTION

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Described herein are systems and methods for identifying and addressing conflicts in a neuromodulation event or series of neuromodulation events. Conflicts in neuromodulation or neurostimulation events or series of events may be related to neuromodulation safety, hardware capabilities, and/or software capabilities. For example, a conflict may be one or more of incompatible electrode configuration(s) EC between stimulation blocks (SB), incompatible stimulation block (SB) timing properties (such as e.g. frequency, pulse width, pulse shape, etc.), incompatible stimulation block (SB) amplitude properties, and/or may relate to the safety or comfortability of the neuro stimulation.

Figure 1:
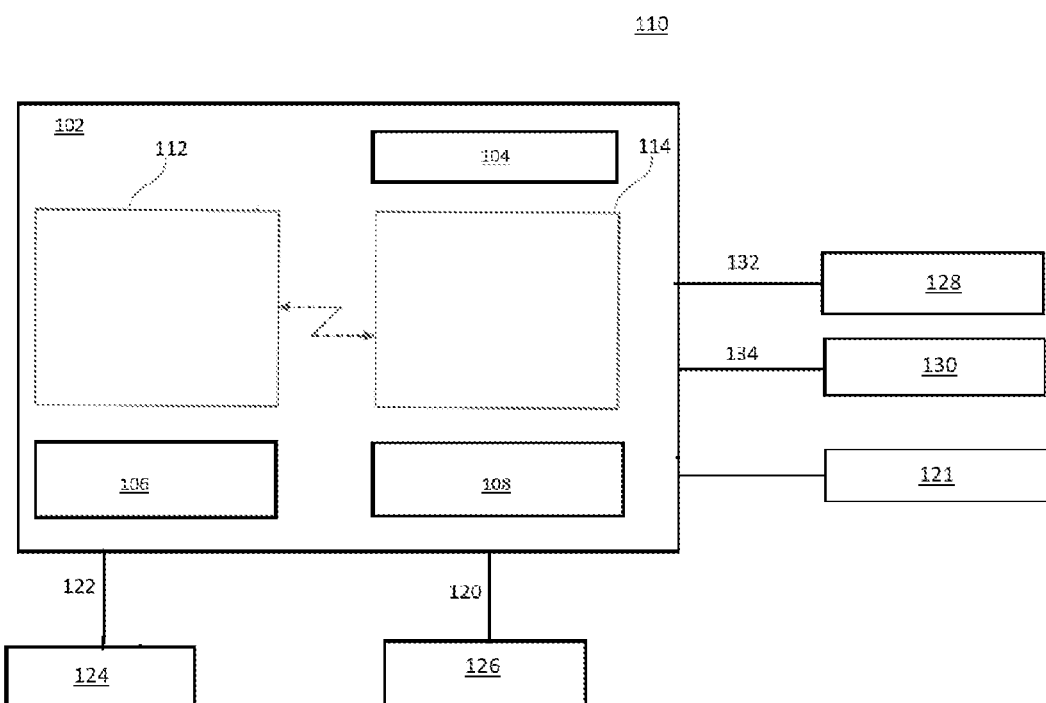
FIG. 1 depicts a schematic overview of an embodiment of the neuromodulation system according to the present invention, with which the method according to the present invention may be performed.
Figure 2:
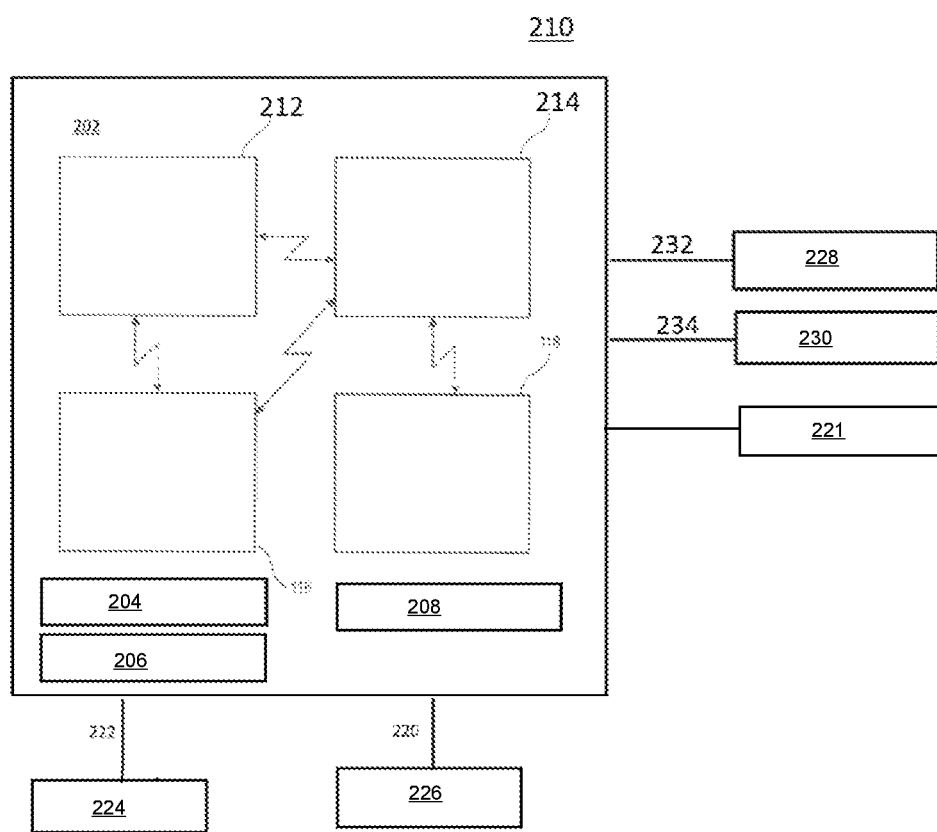
FIG. 2 depicts a schematic overview of a further embodiment of the neuromodulation system according to the present invention, with which the method according to the present invention may be performed.
Figure 3:
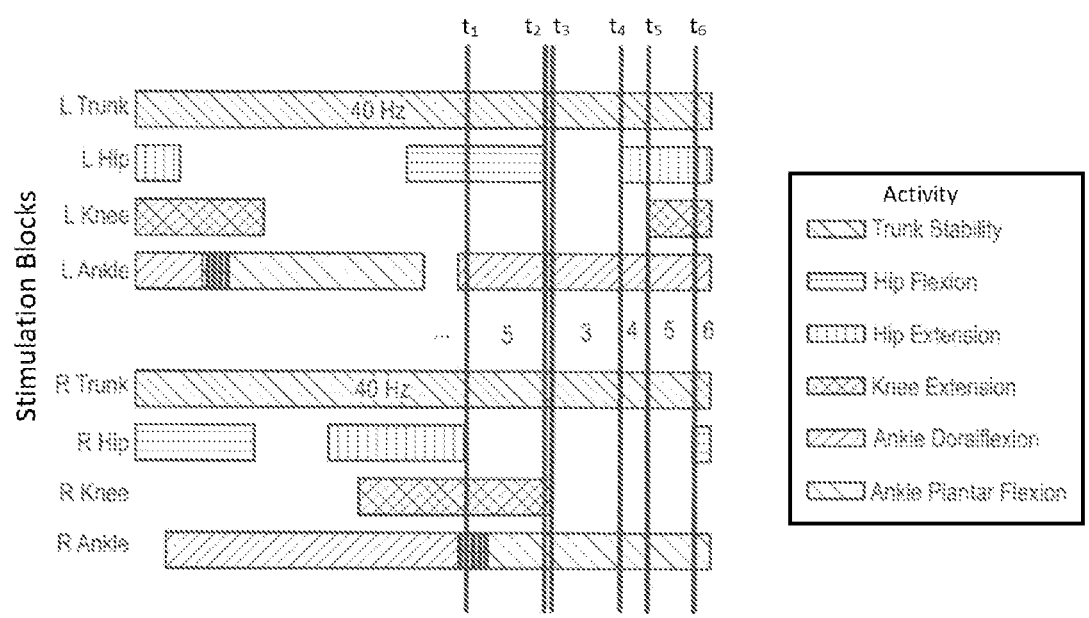
FIG. 3 depicts a schematic overview of a series of neuromodulation events.
Figure 4:
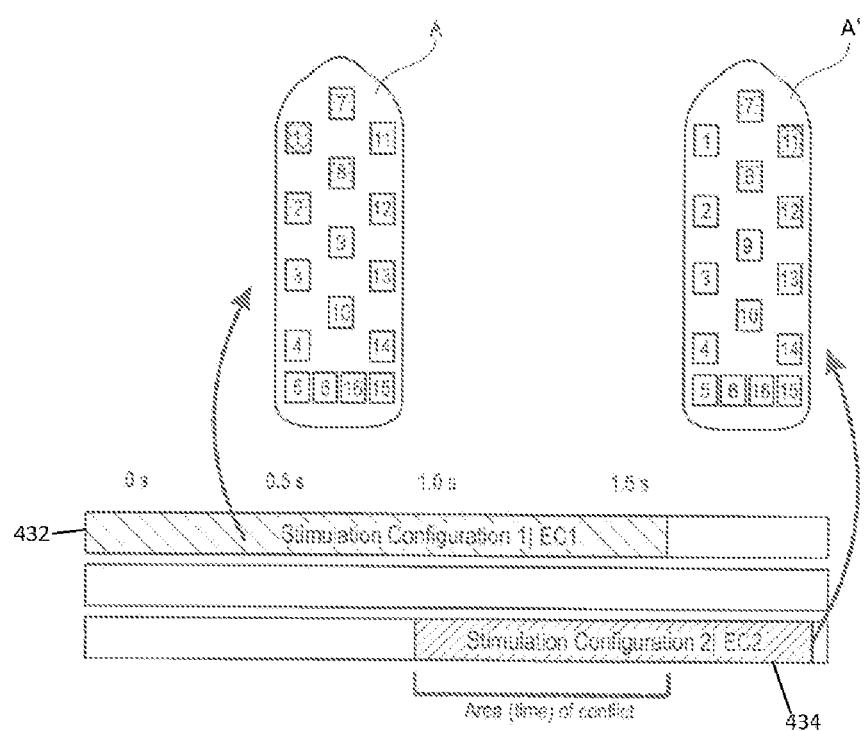
FIG. 4 depicts a schematic drawing of a series of neurostimulation events having the same dependency on certain electrodes of an array at a given time point, leading to conflict(s)
Figure 5:
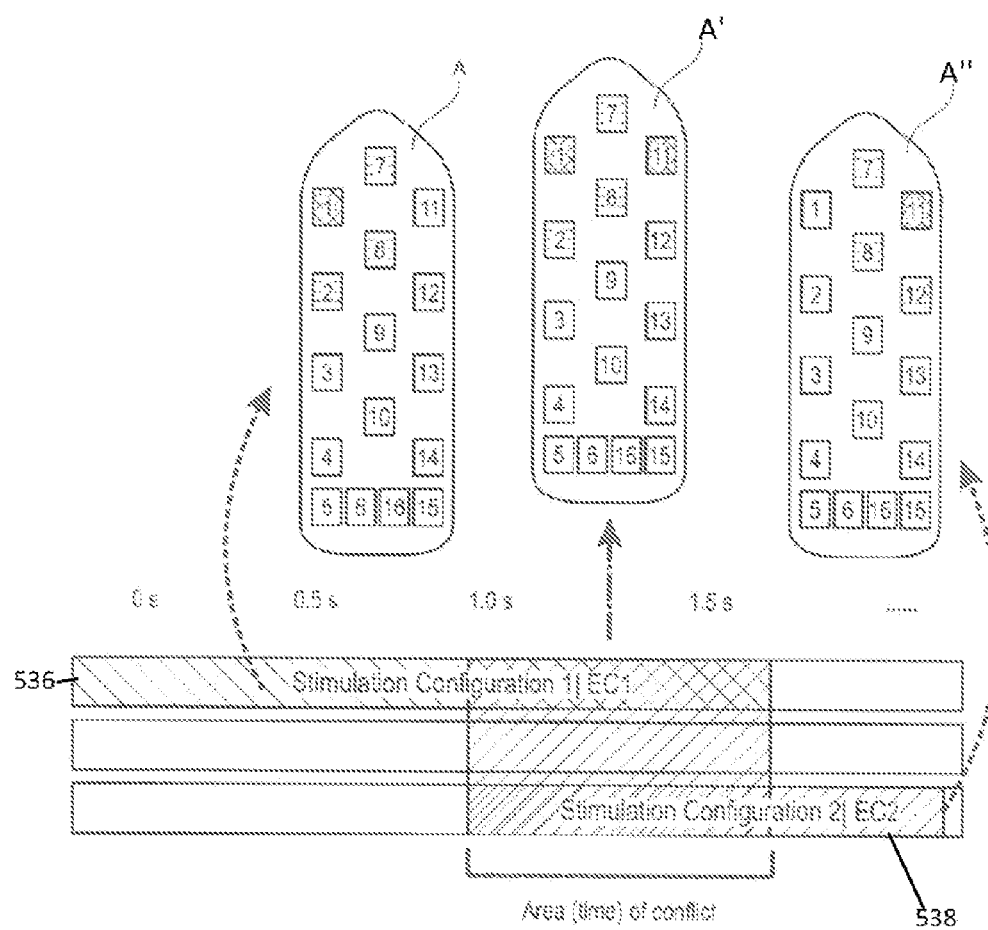
FIG. 5 depicts an exemplary embodiment of merging of two electrode configurations that would otherwise conflict, with the system disclosed in FIG. 2.
Figure 6:
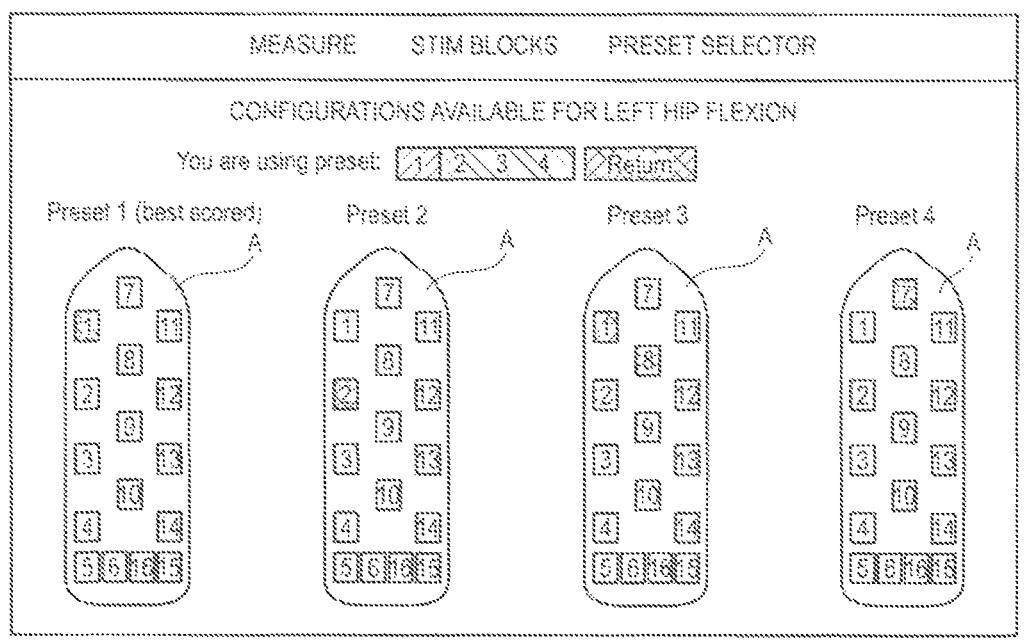
FIG. 6 depicts an exemplary embodiment of the visual output provided by the output means of the system disclosed in FIG. 2.

A neuromodulation event or series of neuromodulation events as shown in FIG. 3 may be analyzed by a neuromodulation system, such as the neuromodulation system shown in FIGS. 1 and 2. As shown in FIGS. 4 and 5, conflicts may be identified and resolution options may be provided by the system shown in FIG. 1 and FIG. 2. Resolution of a conflict may be provided manually, semi-automatically, or automatically using one or more of a plurality of solutions including, but not limited to, pulse interleaving, merging, amendment based on a Pseudo-Hamming Distance Criterion, and/or through the amendment of timing properties such as e.g. frequency, pulse width, pulse shape). In some aspects, resolution may be provided through the presentation of one or more preset neuromodulation events as shown in FIG. 6. In some aspects, identification of the conflict may be output via a visual display as shown in FIGS. 7, 10, 11, and 13. In additional aspects, spacing between pulses may be analyzed using the neuromodulation system shown in FIGS. 1 and 2 as seen by the matrix of FIG. 8. An internal acceptable variation to the end use of the frequency as used in the electrodes of the neuromodulation system shown in FIGS. 1 and 2 is shown in FIG. 9. In some aspects, the neuromodulation system shown in FIGS. 1 and 2 may include a training module (not shown). As shown in FIG. 12, such a training module may be used to inform a user of what stimulation frequency constraints exist while he/she is configuring the stimulation frequency. Exemplary methods as used by the neuromodulation system of FIGS. 1 and 2 for the identification and rectification of conflicts are shown in FIGS. 14 to 16.

FIG. 1 shows a schematic overview of an embodiment of the neuromodulation system 110 according to the disclosed embodiments, with which the methods according to the disclosed embodiments may be performed.

The system 110 may include a device 102 with an input module 112, an analyzing module 114, memory 104, a processor 106, and a communication subsystem 108, though other components and modules may also be included. For example, system 110 may further include a controller, a microcontroller, a telemetry system and/or a training device, and combinations thereof. In some aspects, as shown in FIG. 1, the device 102 may be coupled to a user input device 121, a display 124, an electrode array 126 comprising one or more electrodes, a pulse generator 128, and one or more sensors 130. While the device 102 is shown with a plurality of peripheral devices, the particular arrangement may be altered such that some or all of the components are incorporated in a single or plurality of devices as desired.

Collectively, the various tangible components or a subset of the tangible components of the neuromodulation system may be referred to herein as "logic" configured or adapted in a particular way, for example as logic configured or adapted with particular software, hardware, or firmware and adapted to execute computer readable instructions. The processors may be single core or multicore, and the programs executed thereon may be configured for parallel or distributed processing. The processors may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration, that is, one or more aspects may utilize ubiquitous, convenient, on-demand network access to a shared pool of configurable computing resources that can be rapidly provisioned and released with minimal management effort or service provider interaction. Clouds can be private, public, or a hybrid of private and public, and may include Infrastructure as a Service (IaaS), Platform as a Service (PaaS) and Software as a Service (SaaS). In some aspects, logic and memory may be integrated into one or more common devices, such as an application specific integrated circuit, field programmable gate array, or a system on a chip.

In some embodiments, device 102 may be any computing or mobile device, for example, mobile devices, tablets, laptops, desktops, PDAs, and the like, as well as virtual reality devices or augmented reality devices. Thus, in some embodiments, the device 102 may include a display and thus a separate display 124 or user input device 121 may not be necessary. In other aspects, the device may be coupled to a plurality of displays.

Memory 104 generally comprises a random-access memory ("RAM") and permanent non-transitory mass storage device, such as a hard disk drive or solid-state drive. Memory 104 may store an operating system as well as the various modules and components discussed herein. It may further include devices which are one or more of volatile, non-volatile, dynamic, static, read/write, read-only, random access, sequential access, location addressable, file addressable and content addressable.

Communication subsystem 108 may be configured to communicatively couple the modules within device 102 as well as communicatively coupling device 102 with one or more other computing and/or peripheral devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

As shown in FIG. 1, the system 110 comprises a device 102 with an input module 112. The input module 112 is configured and arranged for inputting a planned neuromodulation event or a series of neuromodulation events. The device 102 further comprises an analyzing module 114. The analyzing module 114 is configured and arranged for analyzing a neuromodulation event or a series of neuromodulation events.

As shown in FIG. 1, the input module 112 is connected to the analyzing module 114 as shown by the dotted by directional arrows. However, such a connection could equally apply to the other components and modules within device 102 all of which may be connected via wired and wireless connections. The connection between the input module 112 and the analyzing module 14 is a bidirectional connection. However, in an alternative embodiment, a unidirectional connection may be implemented (from the input module 112 to the analyzing module 114 and/or from the analyzing module 114 to the input module 112). In some embodiments, the input module 112 is connected to the analyzing module 114 by a wireless link facilitated through communication subsystem 108. In some aspects, one or more of the components and modules within the device 102 may be on the same or different devices, for example a plurality of modules may be located on the same chip. .

Communication within the system 110 may occur locally or over one or more public/private/hybrid networks 120, 122, 132, 134 among others including one or more of a wireless network, a wired network, or a combination of wired and wireless networks. Suitable networks include, but are not limited to, public, private or hybrid networks including the Internet, a personal area network, a LAN, a WAN, or a WLAN. Information can further be received or transmitted over cellular networks either directly or through a base station and through the cloud. In other aspects input module 112 and analyzing module 114 may exist on the same processor. In further embodiments, they may exist in different devices and be communicatively coupled by a cable-bound connection. For example, in some aspects input module 112 and analyzing module 114 may exist on separate devices, with each device having a processor, memory and communication subsystem and the two devices may be commutatively coupled using a wired or wireless connection as described above.

In some embodiments, the input module 112 can input a planned neuromodulation event or a series of neuromodulation events. Such inputs may be received from one or more sources including, but not limited to, a user selecting one or more predesigned configurations or through input of a customized stimulation program. Further in some embodiments, the input module 112 can forward a planned neuromodulation event or a series of neuromodulation events to the analyzing module 114. Also, in some embodiments, the analyzing module 114 can analyze the planned neuromodulation event or a series of neuromodulation events regarding one or more possible neuromodulation conflict(s).

In some embodiments (not depicted in FIG. 1), system 110 could comprise more than one input module 112, and system 110 could comprise more than one analyzing module 114. The system 110 can be configured for a semi-automatic correction of a neuromodulation conflict. The system 110 can be configured for automatic correction of neuromodulation conflict. A neuromodulation conflict may be detected when the planned neuromodulation event or a series of neuromodulation events requires an impossible electrode configuration. More than one neuromodulation conflict can be detected when the planned neuromodulation event or a series of neuromodulation events requires an impossible electrode configuration. More than one neuromodulation conflict can be detected which are not related to electrode configuration.

Conflicts may be related to at least one of neuromodulation safety, hardware capabilities, software capabilities, and combinations thereof. For example, a conflict may be one or more of incompatible electrode configuration(s) EC between stimulation blocks SB, incompatible stimulation block SB timing properties (such as e.g. frequency, pulse width, pulse shape), incompatible stimulation block SB amplitude properties and/or may relate to the safety or comfortability of the neurostimulation. Identified conflicts may be addressed by one or more of amending the planned neuromodulation event or a series of neuromodulation events based on a Pseudo-Hamming Distance Criterion, allowing some pulse overlap and/or adapting the pulse shape; amending incompatible stimulation block SB timing properties (such as e.g. frequency, pulse width, pulse shape); replacing the planned neuromodulation event or series of neuromodulation events with one of alternative Presets instead; allowing custom pulse overlap rules; adapting the pulse shape; lowering the amplitude; assessing electrode stability; assessing the patient's response to stimulation; amending the VRAM available and/or the computation time; and/or issuing an alert and allowing the user to modify the programming.

FIG. 2 shows a schematic overview of a further embodiment of the neuromodulation system 210 according to the present invention, with which the methods according to the disclosed embodiments may be performed. The system 210 may include a device 202 with an input module 212, an analyzing module 214, memory 204, a correction module 116, an output means 118, processor 206, and a communication subsystem 208, though other components and modules may also be included. For example, a controller, a microcontroller, a telemetry system and/or a training device may be implemented in the system 210. In some aspects, as shown in FIG. 2, the device 202 may be coupled to a user input device 121, a display 224, an electrode array 226 comprising one or more electrodes, a pulse generator 228, and one or more sensors 230. While the device 102 is shown with a plurality of peripheral devices, the particular arrangement may be altered such that some or all of the components are incorporated in a single or plurality of devices as desired. Device 202 is a non-limiting example of device 102 and as such may include the same or similar components as described above.

In some embodiments, device 202 may be any computing or mobile device, for example, mobile devices, tablets, laptops, desktops, PDAs, and the like, as well as virtual reality devices or augmented reality devices. Thus, in some embodiments, the device 202 may include a display and user input device and thus a separate display 224 or user input device 221 may not be necessary.

Memory 204 generally comprises a random-access memory ("RAM") and permanent non-transitory mass storage device, such as a hard disk drive or solid-state drive. Memory 204 may store an operating system as well as the various modules discussed herein. It may further include devices which are one or more of volatile, non-volatile, dynamic, static, read/write, read-only, random access, sequential access, location addressable, file addressable and content addressable.

Communication subsystem 208 may be configured to communicatively couple the modules within device 202 as well as communicatively coupling device 202 with one or more other computing devices. Such connections may include wired and/or wireless communication devices compatible with one or more different communication protocols including, but not limited to, the Internet, a personal area network, a local area network (LAN), a wide area network (WAN) or a wireless local area network (WLAN). For example, wireless connections may be WiFi, Bluetooth®, IEEE 802.11, and the like.

The system 210 comprises the structural and functional features as disclosed for neuromodulation system 110 disclosed in FIG. 1. The corresponding references are indicated as 200+x (e.g. input module 212 or memory 204). Accordingly, device 202 may share features with device 102 described above, memory 204 may share features with memory 104 described above, processor 206 may share features with processor 106 described above, and communication subsystem 208 may share features with communication subsystem 108.

The neurostimulation system 210 may further comprise a correction module 116. In some embodiments, the neurostimulation system 210 comprises more than one correction module 116. In some embodiments, the neurostimulation system 210 further comprises output means 118. The correction module 116 is connected to the input module 212 and the analyzing module 214.

In some embodiments, the connection between the correction module 116 and the input module 212 and the correction module 116 and the analyzing module 214 is a bidirectional and wireless connection through communication subsystem 208. Communication within the system 210 may occur locally or over one or more public/private/hybrid networks 220, 222, 232, 234 including one or more of a wireless network, a wired network, or a combination of wired and wireless networks. Suitable networks include, but are not limited to, public, private or hybrid networks including the Internet, a personal area network, a LAN, a WAN, or a WLAN. Information can further be received or transmitted over cellular networks either directly or through a base station and through the cloud. In other aspects, input module 212, analyzing module 214, correction module 116, and output means 118 may exist on the same processor. In further embodiments, input module 212, analyzing module 214, correction module 116, and output means 118 may exist in one or more devices and be communicatively coupled by a cable-bound connection. For example, in some aspects input module 212, analyzing module 214, correction module 116, and output means 118 may exist on separate devices, with each device having a processor, memory and communication subsystem and the two or more devices may be commutatively coupled using a wired or wireless connection as described above.

As depicted in FIG. 2, the output means 118 may be connected to the analyzing module 214. In some embodiments, the output means 118 is an output module. In some embodiments, the connection between the output means 118 and the analyzing module 214 is a bidirectional and wireless connection. However, in an alternative embodiment, a unidirectional and/or cable-bound connection between the output means 118 and the analyzing module 214 may be implemented. In an alternative embodiment, the output means 118 may additionally be connected to the input module 212 and/or the correction module 116 (via bidirectional or unidirectional connection and/or wireless or cable-bound connection).

In some embodiments, the correction module 116 amends the planned neuromodulation event or a series of neuromodulation events. In some embodiments, when a neurostimulation conflict is detected, the neuromodulation event or a series of neuromodulation events is/are amended such that the neuromodulation conflict is avoided as described in further detail below. In some embodiments, the output means 118 provides at least partially a visual output of the analysis performed by the analyzing module 214. In an alternative embodiment, the output means 118 provides, at least partially, the planned neuromodulation event or a series of neuromodulation events and/or the neuromodulation conflict(s) and/or the correction of the planned neuromodulation event or a series of neuromodulation events. In some aspects, the visual output can be sent to the display 224.

In some embodiments (not shown in FIG. 2), system 210 can also include multiple correction modules, and system 210 may also comprise multiple output means. The system (e.g. system 110 and/or system 210) may perform a method for performing neuromodulation comprising at least the following steps: receiving a planned neuromodulation event or a series of neuromodulation events, analyzing the planned neuromodulation event or a series of neuromodulation events, wherein the analyzing includes the analysis whether the planned neuromodulation event or a series of neuromodulation events comprises one or more possible neuromodulation conflict(s).

In some embodiments, the method may further comprise correcting the neuromodulation event or a series of neuromodulation events such that the one or more possible neuromodulation conflict(s) is/are avoided.

In general, the system (e.g. system 110 and/or system 210) and the method may avoid and/or solve the conflict(s) may by amending incompatible electrode configuration(s) EC between stimulation blocks SB and/or amending incompatible stimulation block SB timing properties (such as e.g. frequency, pulse width, pulse shape) and/or by amending incompatible stimulation block SB amplitude properties and/or by assessing the safety or comfortability of the neurostimulation and/or by amending software limitations.

FIG. 3 shows a schematic overview of a series of neuromodulation events of different stimulation blocks SB. The series of neuromodulation events can also be referred to as stimulation program and/or stimulation partiture.

A stimulation block may determine an electrode configuration and/or stimulation configuration, and/or an amplitude/intensity of stimulation and a pulse train, wherein a pulse train may be defined as a temporal arrangement of stimulation events. Different stimulation blocks need to be stimulated during movement (e.g. a gait cycle) consequentially and/or at least partially simultaneously with different pulsed electrical waveforms at different frequencies and amplitudes, sometimes with different pattern of pulses, in order to reproduce a movement, e.g. a gait cycle comparable to a healthy subject.

As illustrated in FIG. 3, the series of neuromodulation events includes multiple time segments (indicated by the vertical lines $t_1$, $t_2$, $t_3$, $t_4$, $t_5$, $t_6$). In some embodiments, the stimulation blocks SB are Left (L) Trunk, Left (L) Hip Flexion, Left (L) Hip Extension, Left (L) Knee, Left (L) Ankle Flexion, Left (L) Ankle Extension, Right (R) Trunk, Right (R) Hip Flexion, Right (R) Hip Extension, Right (R) Knee, Right (R) Ankle Flexion, Right (R) Ankle Extension.

In each time segment, the combination of active stimulation blocks SB each targeting a specific muscle group may be fixed. In some embodiments, the first time segment $t_1$ drawn has 5 stimulation blocks SB active simultaneously (Left (L) Trunk and Right (R) Trunk counted as one). In some embodiments, the second time segment $t_2$ drawn has 4 stimulation blocks SB active simultaneously (Left (L) Trunk and Right (R) Trunk counted as one). In some embodiments, the third time segment $t_3$ drawn has 3 stimulation blocks SB active simultaneously (Left (L) Trunk and Right (R) Trunk counted as one). In some embodiments, the fourth time segment $t_4$ drawn has 4 stimulation blocks SB active simultaneously (Left (L) Trunk and Right (R) Trunk counted as one). In some embodiments, the fifth time segment $t_5$ drawn has 5 stimulation blocks SB active simultaneously (Left (L) Trunk and Right (R) Trunk counted as one). In some embodiments, the sixth time segment $t_6$ drawn has 6 stimulation blocks SB active simultaneously (Left (L) Trunk and Right (R) Trunk counted as one). As shown in the legend, each stimulation block is directed towards stimulating a particular action or activity.

FIG. 4 shows a schematic drawing of a series of neurostimulation events having the same dependency on certain electrodes of an array (see e.g. electrode array 226 in FIG. 2) at a given time point, with the dependency of the first stimulation block shown at A and the second stimulation block shown at A', leading to a conflict, where A and A' are different configurations of the same electrode array.

In some embodiments, the neuromodulation system 210 disclosed in FIG. 2 is applied. FIG. 4 illustrates two electrode configurations EC1, EC2 (also referred to as stimulation configurations) and an electrode array A, A' comprising 16 electrodes 1-16. In an alternative embodiment, the electrode array A, A' may comprise fewer or more than 16 electrodes.

In some embodiments, the series of neurostimulation events comprises two different electrode configurations EC1 and EC2 for two different stimulation blocks SB1 432 and SB2 434. Stimulation block 1 432 is requested to be stimulated according to electrode configuration 1 EC1. Stimulation block 2 434 is requested to be stimulated according to electrode configuration 2 EC2. The electrodes used by the stimulation configuration are shown in hatching with A and A' indicating different patterns of use in the same array. For example, in array A, as shown by the various hatch patterns, electrodes 1, 2, 7, and 8 will be used for stimulation configuration 1. As shown in A', electrodes 7, 8, 11 and 12 will be used for stimulation configuration 2. Thus, FIG. 4 illustrates that the two electrode configurations EC1 and EC2 both use electrode 7 and electrode 8 of the electrode array.

As shown in the stimulation configuration, the two stimulation blocks SB1 432, SB2 434 have overlapping periods of use from 1.0 s to 1.5 s. The analyzing module 114 of the system 110 would thus detect a neuromodulation conflict of the planned series of neuromodulation events. Correction module 116 of the system 210 may amend the planned series of neuromodulation events such that the neuromodulation conflict is avoided. Correction may be made manually, automatically, or semi-automatically.

In some embodiments (not shown in FIG. 4), the correction module 116 amends the planned series of neuromodulation events by providing at least one alternative electrode configuration EC (see, e.g. FIG. 6). Alternatively, and/or additionally, the correction module 116 could amend the planned series of neuromodulation events by keeping the electrode configurations EC1 and EC2 but interleaving pulses, thus by avoiding pulse overlap. If the stimulation pulses are interleaved in a way that fully avoids overlap, then the shared electrodes will not be requested by both stimulation block 1 and stimulation block 2 at the same time. This pulse interleaving could be done with any method avoiding pulse overlap, e.g. Pulse Train Scheduling. Alternatively, and/or additionally, the correction module 116 could amend the planned series of neuromodulation events by merging electrode configuration EC1 and electrode configuration EC2, cf. FIG. 5.

FIG. 5 shows an example of merging of two electrode configurations EC1 and EC2 that would conflict as electrodes 7 and 8 would be used in both configurations from 1.0 s to 1.5 s as shown in A and A". In order to overcome this conflict, the system 210 disclosed in FIG. 2 merges two electrode configurations EC1 and EC2 as shown at A' via the correction module 116 that amends the planned series of neuromodulation events.

In some embodiments, the correction module 116 provides an automated merging of electrode configurations EC1 and EC2 and balance amplitudes. In some embodiments, during the period of overlap, the electrode configurations EC1 and EC2 are merged. The merged stimulation block SB delivers a single stimulation, exciting both the nerve fibers targeted by stimulation block SB1 536 and the nerve fibers targeted by stimulation block SB2 538 at the same time.

However, the achieved stimulation for the nerve fibers targeted by stimulation block SB1 and for the nerve fibers targeted by stimulation block SB2 may depend on both the amplitude and on the frequency used. Thus, merging the electrode configurations EC1, EC2 of both stimulation blocks SB1, SB2 may be implemented if the frequencies and amplitudes of both stimulation blocks SB1, SB2 match, are nearly identical, or are identical.

In some aspects, the correction module 116 may amend the neuromodulation event or series of neuromodulation events by merging the electrode configurations if the conflict between the planned neuromodulation event or series of neuromodulation events meets specific criteria. For example, the stimulation events may be merged if the planned event meets particular criteria. In some embodiments, the stimulation configuration may be merged if a particular tolerance margin is obtained. In some embodiments, the stimulation configurations can be merged if at least one of the frequency of stimulation block SB1 is within a ±15 Hz of the frequency of stimulation block SB2 or the amplitude of stimulation block SB1 is within a ±2 mA of the amplitude of stimulation block SB2.

Depending on the stimulation frequencies used for stimulation block SB1 and stimulation block SB2, only part of their pulses may overlap in time. Therefore, the electrode sharing conflict only emerges during those periods of pulse overlap. In some aspects, the system may therefore merge both electrode configurations EC1, EC2 into one configuration when such a conflict arises, i.e. for some specific colliding pulses.

The amplitudes can be balanced to preserve either the charge balancing or the electrical field. Summing the current on the shared electrode will preserve the charge balancing but may heavily impact the electrical field. For instance, in the example shown in FIG. 5: stimulation block SB1 uses electrode 1 as a cathode at −9 mA and electrode 2, electrode 7 and electrode 8 as anodes at 3 mA each. Stimulation block SB2 uses electrode 11 as a cathode at −18 mA and electrode 12, electrode 7 and electrode 8 as anodes at 6 mA each. Summing the current will result in:

Electrode 1: −9 mA
Electrode 11: −18 mA
Electrode 2: 3 mA
Electrode 12: 6 mA
Electrodes 7, 8: 9 mA Instead, choosing to use the average of the current on the shared electrode would result in:

Electrode 1: −9 mA
Electrode 11: −18 mA
Electrode 2: 3 mA
Electrode 12: 6 mA
Electrodes 7, 8: 4.5 mA The electrical field is closer to the electrical field generated by each stimulation block SB taken separately but the charge balancing is lost. However, if the amount of corrupted pulse for stimulation block SB1 and stimulation block SB2 is sufficiently low, e.g. below a threshold, then the grounding time could accommodate for the loss of charge balancing.

FIG. 6 shows an example of the visual output of particular electrode configurations a user can select as provided by the output means 118 of the system 210 disclosed in FIG. 2. In some embodiments, the output means 118 provides different electrode configurations EC to achieve a certain muscular response.

For example, in the event of a conflict, as disclosed in FIG. 4, the stimulation configuration inputted may be replaced with one of alternative Presets instead. Thus, in some embodiments, the output means 118 provides (at least partially) a visual output of the correction of the conflict of the planned series of neuromodulation events disclosed in FIG. 4. In some embodiments, four Presets may be available, out of a maximum amount of Presets, which may be five. Moreover, using a graphical user interface, a more advanced user could also replace the inputted stimulation configuration with a custom electrode configuration. Alternatively, as for the solution merging electrode configurations, the system could also use an alternative stored Preset stimulation configuration for the pulses of stimulation block SB1 and stimulation block SB2 that overlap in time.

In general, the output means 118 and the analyzing module 214 may function online or offline as each pulse can be linked to an index. Each pulse needing a non-default stimulation configuration may have its index and the associated Preset stimulation configuration transmitted to the stimulation system along with the stimulation program.

In addition to conflicts depending on electrode configurations, the stimulation partiture could also include stimulation blocks that are intended to be active at the same time yet use conflicting properties such as their frequencies or pulse shape. Moreover, a method avoiding pulse overlap may be applied to limit the interference between the stimulation blocks. Each time segment can be translated into an input combination for the method avoiding pulse overlap, (e.g. 20, 40, 75 Hz). The method avoiding pulse overlap may find a solution avoiding pulse overlap. However, some combinations may not have a solution and are marked as non-solutions. Thus, if such a combination is inputted on the partiture by the user, it will result in a conflict as shown below.

Figure 7:
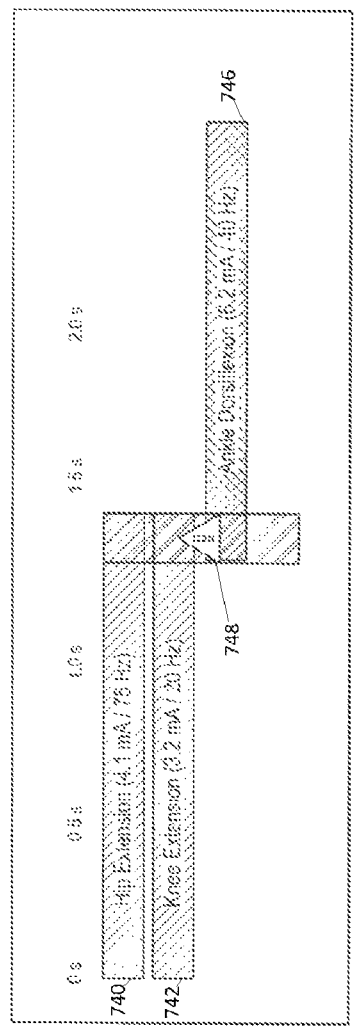
FIG. 7 depicts an exemplary embodiment of incompatible stimulation block timing properties, analyzed with the system disclosed in FIG. 2, provided as visual output by the output means.

FIG. 7 shows visual output provided by the output means 118 of an analysis performed by the analyzing module 114, 214, of the system 110, 210 disclosed in FIGS. 1 and 2. In some embodiments, the system 210 may analyze and correct pulse overlap. In an alternative embodiment, the system 110, 210 may analyze and correct inter alia pulse overlap.

FIG. 7 illustrates an example of incompatible stimulation block SB timing properties, analyzed with the system 110, 210 disclosed in FIGS. 1 and 2 provided as visual output by the output means 118.

In some embodiments, the system 110, 210 is configured for avoiding pulse overlap, and is applied to limit the interference between the stimulation blocks SB1 (including the hip and knee extension stimulation) and SB2 (including the ankle dorsiflexion stimulation). As shown at 748, an alert is shown indicating a conflict prior to 1.5 s.

In some aspects, the correction module 116 may provide a plurality of solutions to correct or overcome the conflict. For example, each time segment could be translated into an input combination avoiding pulse overlap (e.g. 20, 40, 75 Hz). However, this solution may not work for all combinations. In other aspects, the correction module 116 may amend the planned neuromodulation event or a series of neuromodulation events based on a Pseudo-Hamming Distance Criterion, allowing some pulse overlap and/or adapting the pulse shape. In other words, in some embodiments, the conflict is avoided by amending incompatible stimulation block SB timing properties (such as e.g. frequency, pulse width, pulse shape) as discussed in further detail below.

Pseudo-Hamming Distance Criterion

For example, a Pseudo-Hamming distance criterion could be applied to determine close-by inputs which are acceptable. In some embodiments, the above-described example with a unique pulse shape and the frequencies (e.g. 20, 40, 75 Hz) is considered. In some embodiments, it is assumed that the possible programmable input frequencies are 20, 40, 50 and 75 Hz. One of the stimulation blocks SB from the combination (e.g. 20, 40, 75 Hz) could have its frequency replaced with a close-by frequency. To determine the close-by frequencies, a pseudo-Hamming distance criterion is used by the system 110, 210:

Changing 1 element by a step of 1 within the list of inputs results in a distance of 1. e.g.

a. changing 40 to 50 Hz.
b. changing 75 Hz to 50 Hz.

Changing 2 elements by a step of 1 within the list of inputs or changing 1 element by a step of 2 within the list of inputs results in a distance of 2. e.g.

a. Changing 40 to 50 Hz and changing 75 to 50 Hz.
    b. Changing 20 to 50 Hz.

Moreover, two modifications with the same Pseudo-Hamming distance may not be equally favorable because the inputs may not be equally spaced. For instance, changing 40 to 50 Hz could be more favorable than changing 75 Hz to 50 Hz. A weighing factor could be taken into account to represent the distance between the steps, i.e. the size of the step. In the end, if the combination (e.g. 20, 40, 75 Hz) does not have a solution avoiding pulse overlap (or meeting an overlap requirement, e.g. 5% of the total number of pulses may overlap), but the close-by combination (e.g. 20, 50, 75 Hz) does have a solution (e.g. it has only 3% of the pulses overlapping), then the Ankle Dorsiflexion frequency of 40 Hz may be replaced with 50 Hz.

Any kind of equation accounting for the frequencies, but also the pulse shape or other parameter may be used to quantify the distance between combinations of input parameters, e.g. frequency input combinations.

Alternatively, the system 110, 210 could propose to replace "flexor" continuous high-frequency stimulation blocks SB by burst stimulation blocks SB which are more (electric) power efficient and could potentially increase stimulation efficacy as well.

Allowing Some Pulse Overlap

For a variable frequency stimulation algorithm allowing custom pulse overlap rules, the following could be used. For example, if the electrode configurations EC do not overlap (i.e. if there is no electrode shared between the stimulation blocks SB), some overlap between stimulation events and/or pulses may be allowed. For instance, the stimulation phase of each stimulation block SB may be allowed to overlap with the post-stimulation phase of any other SB. Thus, the combination (20, 40, 75) Hz, which may not have any solutions avoiding pulse overlap, may now have solutions with partial and/or limited overlap. The user can be presented with options indicating the percentage of overlapping pulses for the different frequencies involved in the desired input combination. Alternatively, the solution may be selected automatically based on predefined criteria, such as selecting the solution with the lowest cumulative overlap percentage.

Adapting The Pulse Shape

If a combination of stimulation blocks SB does not have a solution respecting the pulse overlap requirements, the timeline may be too crowded. An exemplary approach to free up time on the timeline is to reduce the pulse duration by adapting its shape. For instance, for biphasic pulses, the post-stimulation phase could be shortened or dropped altogether.

The hardware may not be able to deliver the stimulation if the amplitude of the planned neuromodulation event or series of neuromodulation events exceeds the hardware capability. Especially in the case of overlapping pulses, partially or fully, the sum of the amplitude from the overlapping pulses may exceed the hardware capability. Additionally, and/or alternatively, the conflict(s) may be based on incompatible stimulation block SB amplitude properties.

The correction module 116 of the neuromodulation system 210 (see e.g. FIG. 2) may amend the planned neuromodulation event or a series of neuromodulation events at least partially based on lowering the amplitude.

Lowering The Amplitude

Additionally, and/or alternatively, the amplitude of one or of several of the stimulation blocks SBs involved in the conflict(s) could be lowered to resolve the conflict.

For example, the conflict may be resolved if the amplitude of all stimulation blocks SBs may all be lowered with the same percentage leading to a total current that is within the current capabilities of the stimulation engine.

Digital-To-Analogue Converter Setting Time

The digital-to-analogue converter used to deliver a precise stimulation current/voltage needs a finite amount of time to change its output value to the newly programmed setting.

In one embodiment, a digital-to-analogue-converter could need up to 200 μs to 1 ms to change a pulse generator output current from one a previous programmed value to the newly desired one. To assess if the digital-to-analogue-converter involved in the neurostimulation program will always have sufficient time to change their output, the following method could be applied:

For all the combinations of two stimulation blocks SB sharing the same current/voltage source, at least one of compute the pulse distance matrix of the two stimulation blocks SB, or check if any value is below a threshold (e.g. 200 μs, 400 μs or 1 ms).

The pulse distance matrix represents the temporal distance between pulse i of stimulation block SB1 and pulse j of stimulation block SB2. An example computed for a stimulation block SB1 at 100 Hz, starting at t=1.65 ms; and a stimulation block 2 at 70 Hz starting at t=0 ms is provided in FIG. 8.

FIG. 8 illustrates that both stimulation blocks SB1, SB2 are using 300 μs stimulation phase, 50 μs inter-phase delay, 900 μs post-stimulation phase. In some embodiments, the threshold to determine if a digital-to-analogue converter has enough time to change its output can be fixed or computed with the involved change of the digital-to-analogue converter output level through a digital-to-analogue converter model applied by the correction module 116. For instance, changing the output from the minimum to half of the maximum may not take as long as changing the output from the minimum (e.g. zero) to the maximum (e.g. full-scale). If the two stimulation blocks SB1, SB2 sharing a current/voltage source have pulses too close in time, their amplitudes could be lowered/modified in order to ensure that the digital-to-analogue converter output has enough time to reach its final value. Alternatively, if the pulse scheduling method can accommodate it, alternative timing solutions can be looked for and selected to increase the distance between the pulses and to ensure that the digital-to-analogue converter output will have enough time to reach its final value. Yet another alternative is to allow a certain amount of pulse corruption that may happen if the digital-to-analogue converter has not enough time to settle its output to the newly desired level, and consequently, the digital-to-analogue converter is still settling while the stimulation pulse is already output.

Embodiments of this disclosure provide solutions where a particular amount of pulse corruption is allowed, for example, if each stimulation block SB in a solution complies with a maximum allowable corruption percentage of all its pulses. Further, the conflict(s) may be avoided by amending and/or assessing the safety or comfortability of the neurostimulation. In some embodiments, each patient may be different and may have a different reaction to neuromodulation, e.g. stimulation.

This reaction may be modelled and/or measured and used to assess the safety or comfortability of a stimulation program by computing e.g. the electrical field resulting from the neurostimulation, the applied charge density or in case of comfortability, measuring the response of a patient to stimulation. A threshold may be applied to those parameters to assess if the neurostimulation is within predefined safety or comfortability limits (e.g. preventing too intense, uncomfortable stimulation).

Grounding Time

The charges injected in the tissue must be recovered through active or passive recuperation to ensure electrode stability and to keep stimulation currents/voltages within the compliance ranges of the pulse generators. More specifically, grounding could help to prevent that an electrode potential exceeds the water window so that electrode stability can be guaranteed. The passive recuperation may be achieved through grounding for a particular amount of time: i.e. grounding the electrodes when no stimulation pulse is output. However, charge recovery is not instantaneous, but the amount of grounding time may be assessed beforehand.

If it is verified that the available grounding time of all timing solutions used in a partiture is sufficient, the stimulation program may be deemed permissible and may be used by the stimulation system (e.g. IPG), else, an alternative stimulation program may be proposed where the partiture does comply with a minimum amount of grounding time for each electrode. Moreover, the distribution of the grounding time in time may also be taken into account to assess if a solution ensures electrode stability during stimulation.

Comfortability

The comfortability could also be assessed by measuring/evaluating the patient's response to a stimulation (e.g. the response to a stimulation block SB, a time segment or a complete partiture). This additional information may be used to further customize the allowable stimulation for the patient. For instance, the ramp up speed used to ramp up the amplitude at the beginning of a stimulation block, and to limit the torque in a joint movement, could be adapted for each patient based on his feedback (e.g. a maximum allowable amplitude ramping speed may be set for each joint of a patient).

Further, the conflict(s) could be avoided by amending software limitations. In some embodiments, the computational power of implantable devices is usually limited because of their low-power properties. To output a stimulation program/partiture, a certain number of steps could be required based on the software implementation. The stimulation program/partiture may create conflicts within the software capabilities which may require a change of the stimulation parameters. The impact of the stimulation program/partiture on the implantable device software can also be assessed beforehand and conflicts can be avoided before the program is released to the stimulation system. Further, the conflict(s) could be avoided by amending the VRAM available and/or the computation time.

VRAM Available

Especially if the stimulation program/partiture is composed of many stimulation blocks, the implantable device might not be able to output the stimulation program because it exceeds its memory capacity. A limitation on the length of the stimulation program/partiture and on the number of used stimulation blocks can be added to the checking criteria to prevent this memory overflow error.

Computation Time

Moreover, to deliver the stimulation a controller, e.g. an implanted microcontroller may perform multiple operations, e.g. sending messages, accessing a look-up table, etc. Usually, the controller scheduling rules are "best-effort": if two tasks have to be performed together, one will be delayed. Those delays may be impacting the neurostimulation, e.g. a pulse could be delayed changing the timing of the stimulation. A minimum amount of time for each task could be implemented. If the stimulation program/partiture inputted results in scheduling conflicts (e.g. overlapping tasks), then the partiture is adapted in order to attribute this minimum amount of time for each task.

In one embodiment, the neuromodulation system 110, 210, in some embodiments the output means 118, comprises a graphical-user-interface for the user to create stimulation partitures. The output means 118 provides at least two pathways for resolving arising conflict(s), including at least one of automatically suggesting and applying an alternative stimulation program, or providing information to the user so that the user can manually perform corrections.

Automatically Providing Alternative Stimulation Program

The system 110, 210 may automatically apply modifications to the stimulation blocks SB/partiture. For instance, the amplitude, the frequency or the pulse width may be changed automatically.

FIG. 9 depicts an exemplary indication of an acceptable variation of the frequency to the end-user. This indication can be communicated by the output means 118 of the system 210. In some embodiments, the correction module 116 may feature a frequency margin/tolerance that, in case of conflicts, it may select any frequency between 72 and 88 Hz to accommodate the user's desired partiture. The frequency margin/tolerance can be visualized as a ±10% indicator while the user selects the frequency on a graphical user interface, provided by the output means 118. In this approach, the user is not shown when conflicts occur and the user is not asked to perform an action. The system 110, 210 can be provided enough freedom and flexibility in user-defined stimulation parameters to find workable solutions.

Semi-Manual Conflict Resolution

Figure 10:
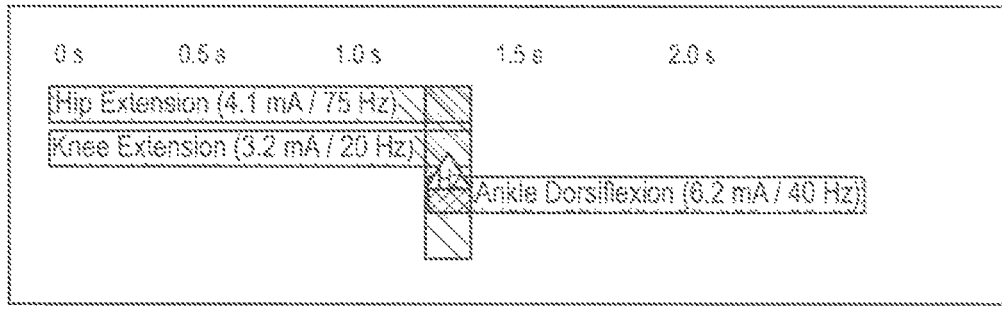
FIG. 10 depict an exemplary embodiment of how the output means of the system could communicate a conflict and an instruction how to resolve this conflict, according to the present invention.

Rather than fully-automatic resolution of conflicts, the output means 118 may provide visual feedback to the user that a conflict exists (or did exist) and a solution needs to be applied (or was provided automatically). Such feedback could be visualized directly on a graphical-user-interface through which the user is creating the stimulation partiture. Possible visualizations and embodiments are shown in FIGS. 7 and 10.

Figure 11:
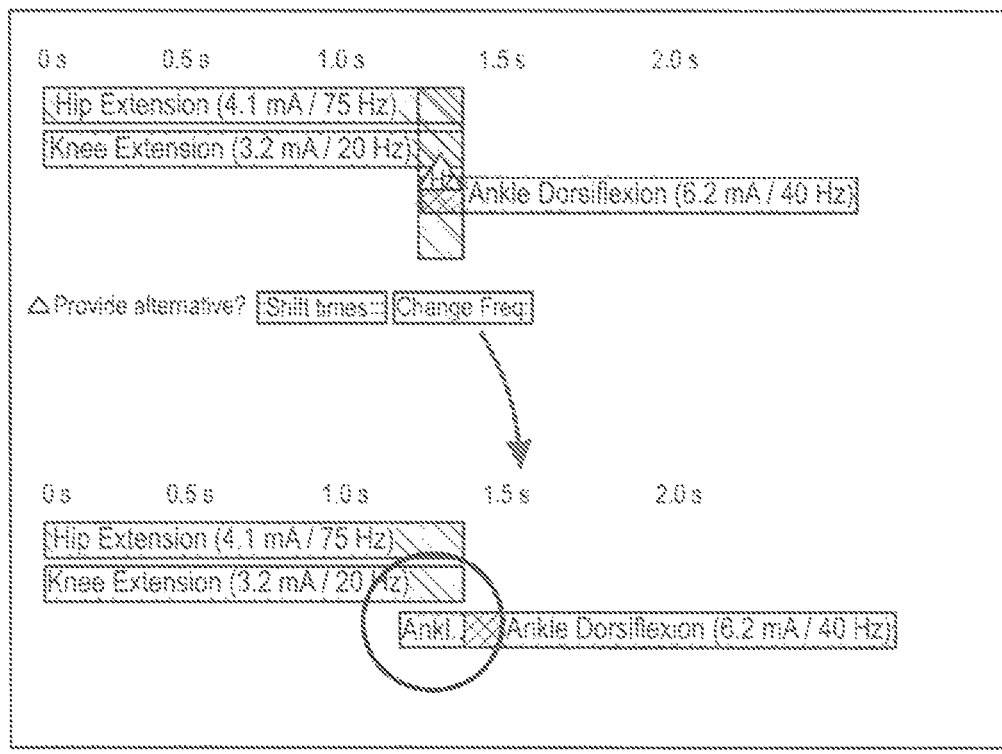
FIG. 11 depicts an exemplary embodiment of how the output means of the system could communicate a conflict and two possible strategies that can be applied by the system to resolve the conflict.
Figure 12:
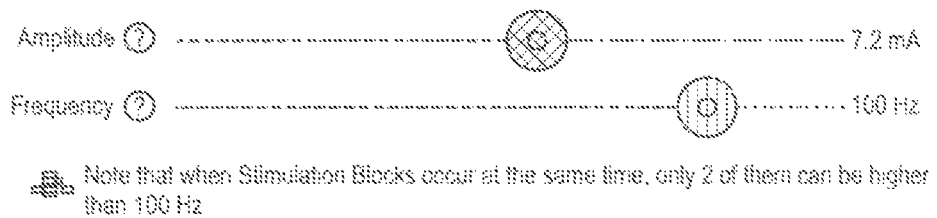
FIG. 12 depicts an exemplary embodiment of how the output means provide visible information on what stimulation frequency constraints exist to a user while he/she is configuring the stimulation frequency.

FIG. 11 illustrates that there are various possible embodiments with different degrees of manual control to the user. For example, the user may be presented options by the output means 118 and he/she may select the desired approach. In some embodiments, the user can be presented two possible strategies/algorithms the correction module 116 can apply to resolve the conflict. Here, the user picks the option to change frequencies after which the correction module 116 creates a second Ankle Dorsiflexion that, during the overlap period, employs a different frequency that is compatible with the other two blocks (the other two being: Hip Extension and Knee Extension).

Stimulation Conflict Prevention

Moreover, rather than combatting the effects, stimulation conflicts could also be prevented from arising initially. This may be implemented by educating the user while he or she is creating stimulation partitures. Hints or instruction messages could be provided using so-called "Just-in-time" information paradigms.

One exemplary embodiment is shown in FIG. 12 when the user is taught what stimulation frequency constraints exist while he/she is configuring the stimulation frequency. In some embodiments, the output means 118 provides a note to instruct the user about the system 110 limitation. In this case, the user must choose a frequency accordingly.

Figure 13:
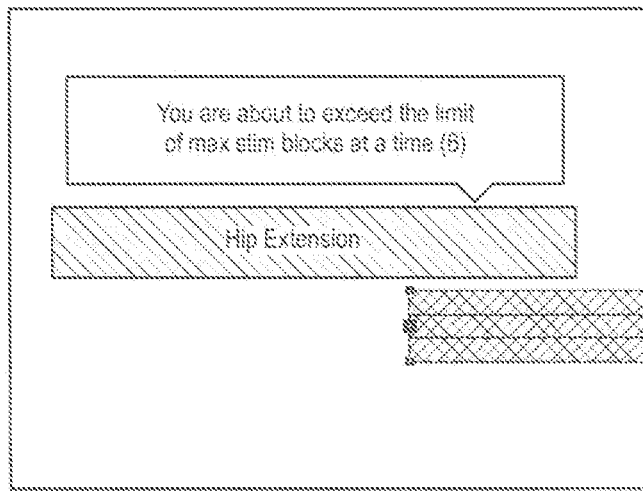
FIG. 13 depicts an exemplary embodiment of how the output means provide visible information on how a user is informed about the systems limitations.
Figure 14:
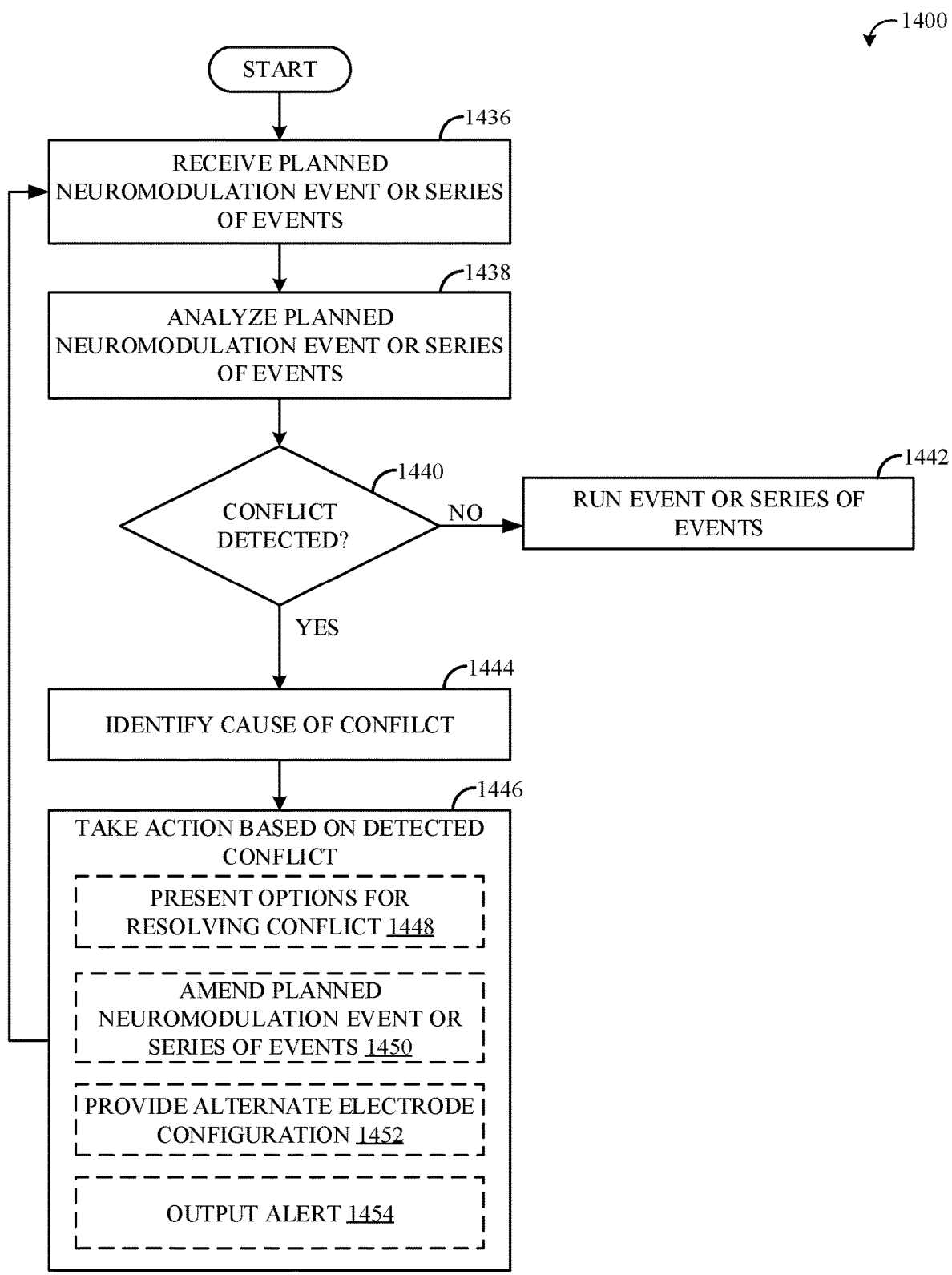
FIG. 14 depicts a flowchart illustrating an example method for identifying and correcting a conflict.

One further exemplary embodiment is shown in FIG. 13 when the user is informed about the systems limitations. In some embodiments, the output means 118 provide a note that the user must avoid placing too many stimulation blocks SB in parallel.

FIG. 14 shows a high-level flow chart 1400 for identifying and rectifying conflicts in a neuromodulation system according to an embodiment. In some embodiments, method 1400 provides the identification of a conflict in a planned neuromodulation event or series of events. Method 1400 is described with regard to systems, components, and methods of FIGS. 1 and 2, though it should be appreciated that method 1400 may be implemented with other systems, components, and methods without departing from the scope of the present disclosure. Method 1400 may be implemented as computer executable instruction in the memory 104, 204 executed by the processor 106, 206 of the device 102, 202.

Method 1400 may begin at 1436 receiving a planned neuromodulation event or series of events. Such an event or series of events may be selected from a preset menu or input manually into, for example, input module 212. The event or series of events can then be analyzed at 1438, for example by analyzing module 214 to identify any potential conflict. Such conflicts include, but are not limited to, one or more of incompatible electrode configuration(s) EC between stimulation blocks (SB), incompatible stimulation block (SB) timing properties (such as e.g. frequency, pulse width, pulse shape), incompatible stimulation block (SB) amplitude properties, and/or may relate to the safety or comfortability of the neurostimulation. If a conflict is not detected at 1440, the device 202 proceeds to run the neuromodulation event or series of events at 1442. If a conflict is detected at 1440, the cause of the conflict is identified at 1444. For example, the method may identify if the conflict is caused by one of neuromodulation safety, hardware capabilities, and/or software capabilities. Once the cause of the conflict is identified, one or more solutions for resolving the conflict may be taken at 1446. Such solutions may be taken individually or jointly in any order.

In some aspects, the options for resolving the conflict may be presented to the user at 1448, for example via a display via an output means such as output means 118. Possible options for resolving the conflict include, but are not limited to, preset configurations, suggestions for pulse interleaving, merging, amendment based on a Pseudo-Hamming Distance Criterion, and/or through the amendment of timing properties such as e.g. frequency, pulse width, pulse shape. In another example, taking an action may include amending the planned neuromodulation event or series of events at 1450. For example, the method may automatically amend the planned neuromodulation event or series of events at 1450 via a correction module, for example correction module 116. In another example, at 1452, the device may provide an alternate electrode configuration at 1452. Such an alternate electrode configuration may be presented as a series of presets as shown at FIG. 6, for example. In other aspects, the alternate electrode configuration may be a merger as shown in FIG. 5. In another example, if a conflict is detected at 1454, the device may output an alert. Such an alert may be auditory and/or visual as known to those of skill in the art. In some aspects, the alert may be presented on the display via output means 118. In some aspects different types of conflicts may generate different types of alerts. The planned neuromodulation event or series of events may be amended automatically, semi-automatically, or manually and then analyzed at 1436 for any further conflicts.

Those having skill in the art will appreciate that there are various logic implementations by which processes and/or systems described herein can be affected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one Application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuits forming a communications device. (e.g., a modem, communications switch, or the like)

It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, are also regarded as included within the subject matter of the present disclosure.

The invention claimed is:

1. A method for performing neuromodulation, the method comprising at least the following steps:
inputting one or more planned neuromodulation events into a memory of a neuromodulation controller; and
analyzing the one or more planned neuromodulation events of a plurality of stimulation blocks;
wherein each of the stimulation blocks includes at least one electrode of an epidural electrode array; and
wherein the stimulation blocks are activated for at least one of treatment of autonomic dysfunction or dysreflexia and restoring the autonomic function of a patient; and
wherein the analyzing step further includes determining whether one or more of the planned neuromodulation events comprises one or more possible neuromodulation conflict(s) between at least two stimulation blocks.

2. The method of claim 1, wherein the one or more possible neuromodulation conflict(s) is/are related to at least one of neuromodulation safety, hardware capabilities, software capabilities.

3. The method of claim 2, wherein the conflict is incompatible electrode configuration between stimulation blocks, incompatible stimulation block timing, or incompatible stimulation block amplitude properties.

4. The method of claim 1, wherein the method further comprises the step of correcting the neuromodulation event or a series of neuromodulation events such that the one or more possible neuromodulation conflict(s) is/are avoided.

5. The method of claim 4, wherein the correction is automatic, semi-automatic, or manual.

6. The method according to claim 4, wherein the correction is selected from merging, interleaving pulses, amending VRAM available, amending computation time, replacing the planned neuromodulation event or series of neuromodulation events with one of an alternative preset, allowing some pulse overlap, or amending the timing properties.

7. The method according to claim 6, wherein the timing properties are frequency, pulse width, and pulse shape.

8. The method according to claim 7, wherein the pulse shape is amended by shortening biphasic pulses in a post-stimulation phase.

9. The method according to claim 6, wherein merging is selected when a frequency of the stimulation blocks in conflict is within 15 Hz.

10. The method according to claim 6, wherein merging is selected when an amplitude of the stimulation blocks in conflict is within 2 mA.

11. The method according to claim 1, wherein when a conflict is identified, the method computes a pulse distance matrix of the at least two stimulation blocks and when a timing between the at least two stimulation blocks is below a threshold, the amplitude of electrodes used by the stimulation blocks is lowered.

12. The method according to claim 1, wherein the autonomic dysfunction comprises at least one of altered or impaired regulation of at least one of blood pressure, heart rate, thermoregulation, respiratory rate, immune system, gastro-intestinal tract, metabolism, electrolyte balance, production of body fluids, pupillary response, bladder function, sphincter function and sexual function.

* * * * *